US012754875B2

(12) United States Patent
Fujita et al.

(10) Patent No.: US 12,754,875 B2
(45) Date of Patent: Oct. 6, 2026

(54) INFORMATION PROCESSING DEVICE, INFORMATION PROCESSING METHOD, COOKING ROBOT, COOKING METHOD, AND COOKING EQUIPMENT

(71) Applicant: SONY GROUP CORPORATION, Tokyo (JP)

(72) Inventors: Masahiro Fujita, Saitama (JP); Michael Siegfried Spranger, Tokyo (JP); Tatsushi Nashida, Kanagawa (JP)

(73) Assignee: SONY GROUP CORPORATION, Tokyo (JP)

(*) Notice: Subject to any disclaimer, the term of this patent is extended or adjusted under 35 U.S.C. 154(b) by 1261 days.

(21) Appl. No.: 17/632,028

(22) PCT Filed: Jul. 27, 2020

(86) PCT No.: PCT/JP2020/028638

§ 371 (c)(1),
(2) Date: Jul. 19, 2022

(87) PCT Pub. No.: WO2021/024829

PCT Pub. Date: Feb. 11, 2021

(65) Prior Publication Data

US 2022/0338671 A1 Oct. 27, 2022

(30) Foreign Application Priority Data

Aug. 8, 2019 (JP) ................................ 2019-145958

(51) Int. Cl.

*G06F 15/02* (2006.01)
*G01N 33/02* (2006.01)
*G06Q 50/12* (2012.01)

(52) U.S. Cl.

CPC .......... *G06F 15/025* (2013.01); *G01N 33/02* (2013.01); *G06Q 50/12* (2013.01)

(58) Field of Classification Search

CPC ...... G16H 20/60; G06F 15/025; G01N 33/02; G06Q 50/12

(Continued)

(56) References Cited

U.S. PATENT DOCUMENTS 9,971,737 B2 * 5/2018 Pinel .................... G06F 40/151
2009/0259687 A1 * 10/2009 Do ...................... G06F 16/9535

(Continued)

FOREIGN PATENT DOCUMENTS

CN 105897932 A 8/2016
CN 107103200 A 8/2017

(Continued)

OTHER PUBLICATIONS

Onishi, The easiest AI <artificial intelligence> Super introduction, Mar. 28, 2018, pp. 149-153 (see International Search Report below for concise relevance).

(Continued)

*Primary Examiner* — Matthew D Sandifer
(74) *Attorney, Agent, or Firm* — Paratus Law Group, PLLC

(57) ABSTRACT

The present technology relates to an information processing device, an information processing method, a cooking robot, a cooking method, and cooking equipment capable of generating a new recipe. An information processing device of one aspect of the present technology generates a new recipe on the basis of chemical structure information representing chemical structures of food ingredients used for cooking, sensing information obtained by measuring flavors of food ingredients using a sensor, and flavor subjective information representing subjective evaluation of people with respect to flavors of food ingredients. The present technology can be applied to a computer prepared in a kitchen.

12 Claims, 30 Drawing Sheets

(58) Field of Classification Search
USPC .......................................................... 708/133
See application file for complete search history.

(56) References Cited

U.S. PATENT DOCUMENTS

| | | | | |
|---|---|---|---|---|
| 2011/0167100 | A1* | 7/2011 | Brodowski | A23L 5/10 708/133 |
| 2013/0149675 | A1* | 6/2013 | Slone | A47J 36/321 434/127 |
| 2013/0149679 | A1 | 6/2013 | Tokuda | |
| 2015/0114236 | A1* | 4/2015 | Roy | A47J 44/00 901/41 |
| 2015/0161912 | A1 | 6/2015 | Bhattacharjya et al. | |
| 2015/0199608 | A1* | 7/2015 | Pinel | G06Q 10/067 706/46 |
| 2015/0294225 | A1 | 10/2015 | Takei | |
| 2016/0081515 | A1* | 3/2016 | Aboujassoum | F24C 7/083 434/127 |
| 2016/0179935 | A1 | 6/2016 | Bhattacharjya et al. | |
| 2016/0278563 | A1 | 9/2016 | Choudhary | |
| 2016/0338545 | A1* | 11/2016 | Shah | A47J 31/52 |
| 2017/0097934 | A1 | 4/2017 | Aso | |
| 2017/0215463 | A1* | 8/2017 | Miller | A23L 33/105 |
| 2018/0084809 | A1* | 3/2018 | Byron | A23L 27/00 |
| 2021/0265036 | A1* | 8/2021 | Lynn | G16H 50/70 |

FOREIGN PATENT DOCUMENTS

| | | | |
|---|---|---|---|
| JP | 2017-506169 | A | 3/2017 |
| JP | 2017-536247 | A | 12/2017 |
| JP | 2019-120485 | A | 7/2019 |
| WO | WO-2016160732 | A1 | 10/2016 |

OTHER PUBLICATIONS

Sep. 29, 2020, International Search Report issued for related PCT application No. PCT/JP2020/028638.

Bellini Mario et al: “Interpreting and Executing Recipes with a Cooking Robot” In: “Springer tracts in advanced robotics”, 2013, Berlin; Heidelberg; New York Springer, 2003-, DE, XP055971439, ISSN: 1610-7438 vol. 88, pp. 481-495, DOI: 10.1007/978-3-319-00065-7_33, * the whole document *.

* cited by examiner

Fig. 2 flavor (flavor) = taste ( taste ) + aroma ( aroma ) + texture ( texture )

INFORMATION PROCESSING DEVICE, INFORMATION PROCESSING METHOD, COOKING ROBOT, COOKING METHOD, AND COOKING EQUIPMENT

CROSS REFERENCE TO PRIOR APPLICATION

This application is a National Stage Patent Application of PCT International Patent Application No. PCT/JP2020/028638 (filed on Jul. 27, 2020) under 35 U.S.C. § 371, which claims priority to Japanese Patent Application No. 2019-145958 (filed on Aug. 8, 2019), which are all hereby incorporated by reference in their entirety.

TECHNICAL FIELD

The present technology particularly relates to an information processing device, an information processing method, a cooking robot, a cooking method, and cooking equipment capable of generating a new recipe.

BACKGROUND ART

There are services of making cooking recipes available. A user can search for a favorite recipe by browsing through categories or inputting the name of a food ingredient as a keyword.

For example, chefs at restaurants are required to not only provide the same dishes according to existing recipes but also create new recipes by devising food ingredients, cooking methods, food presentation methods, and the like.

CITATION LIST

Patent Literature

PTL 1

Japanese Translation of PCT Application No. 2017-506169

PTL 2

Japanese Translation of PCT Application No. 2017-536247

SUMMARY

Technical Problem

It is not easy to continuously create new recipes due to the perpetuation of fixed ideas according to common practice, culture, and the like in cooking or a fixed ideas based on experiences.

The present technology has been made in view of such a situation, and makes it possible to create a new recipe.

Solution to Problem

An information processing device of a first aspect of the present technology includes a recipe generation unit configured to generate a new recipe on the basis of chemical structure information representing chemical structures of food ingredients used for cooking, sensing information obtained by measuring flavors of food ingredients using a sensor, and flavor subjective information representing subjective evaluation of people with respect to flavors of food ingredients.

A cooking robot of a second aspect of the present technology and cooking equipment of a third aspect include a control unit configured to perform cooking on the basis of recipe data representing a new recipe generated on the basis of chemical structure information representing chemical structures of food ingredients used for cooking, sensing information obtained by measuring flavors of food ingredients using a sensor, and flavor subjective information representing subjective evaluation of people with respect to flavors of food ingredients.

BRIEF DESCRIPTION OF DRAWINGS

FIG. 2 is a diagram illustrating an example of components of a flavor.

DESCRIPTION OF EMBODIMENTS

<Overview of Present Technology>

The present technology is a technology for generating a new recipe for cooking and presents the generated new recipe for cooking to a user such as a chef. Here, a new recipe means a recipe different from recipes which are generated recipes which are already being prepared. New recipes include a recipe in which at least any of elements constituting the recipe are different from those of recipes which are generated recipes which are already being, such as a recipe having different food ingredients or a recipe having a different cooking method. A dish reproduced on the basis of a new recipe is different from a dish reproduced on the basis of a recipe prepared in advance.

To generate a recipe, chemical structure information representing chemical structures of food ingredients used for cooking, sensing information obtained by measuring flavors of food ingredients using a sensor, and flavor subjective information representing a subjective evaluation of a person with respect to flavors of food ingredients are used. In addition, information representing relations between the chemical structure information, the sensing information, and the flavor subjective information may be used.

For example, when information about subjective evaluation of flavors is input as a condition, sensing information corresponding to the input subjective evaluation is specified and chemical structure information corresponding to the specified sensing information is specified. Food ingredients are selected on the basis of the specified chemical structure information and a recipe using these food ingredients is generated.

A chef who has received a presentation of a recipe can perform cooking according to the presented recipe. Further, the chef can create a new recipe by himself/herself using the presented recipe as a hint. The present technology can also be a technology for presenting information that triggers creation of a new recipe.

A recipe generated by the present technology is used not only by being presented to a chef and the like but also used to control a cooking robot. A cooking robot is a robot that autonomously operates on the basis of recipe data and completes a dish by performing cooking.

The operation of the cooking robot is controlled on the basis of a new recipe and thus a new dish is made by the cooking robot.

Hereinafter, embodiments of the present technology will be described. Note that the description will be given in the following order.

1. Presentation of recipe
2. Generation of recipe
3. Configuration and operation of each device
4. Example of control of cooking robot
5. Other examples <Presentation of Recipe>

Figure 1:
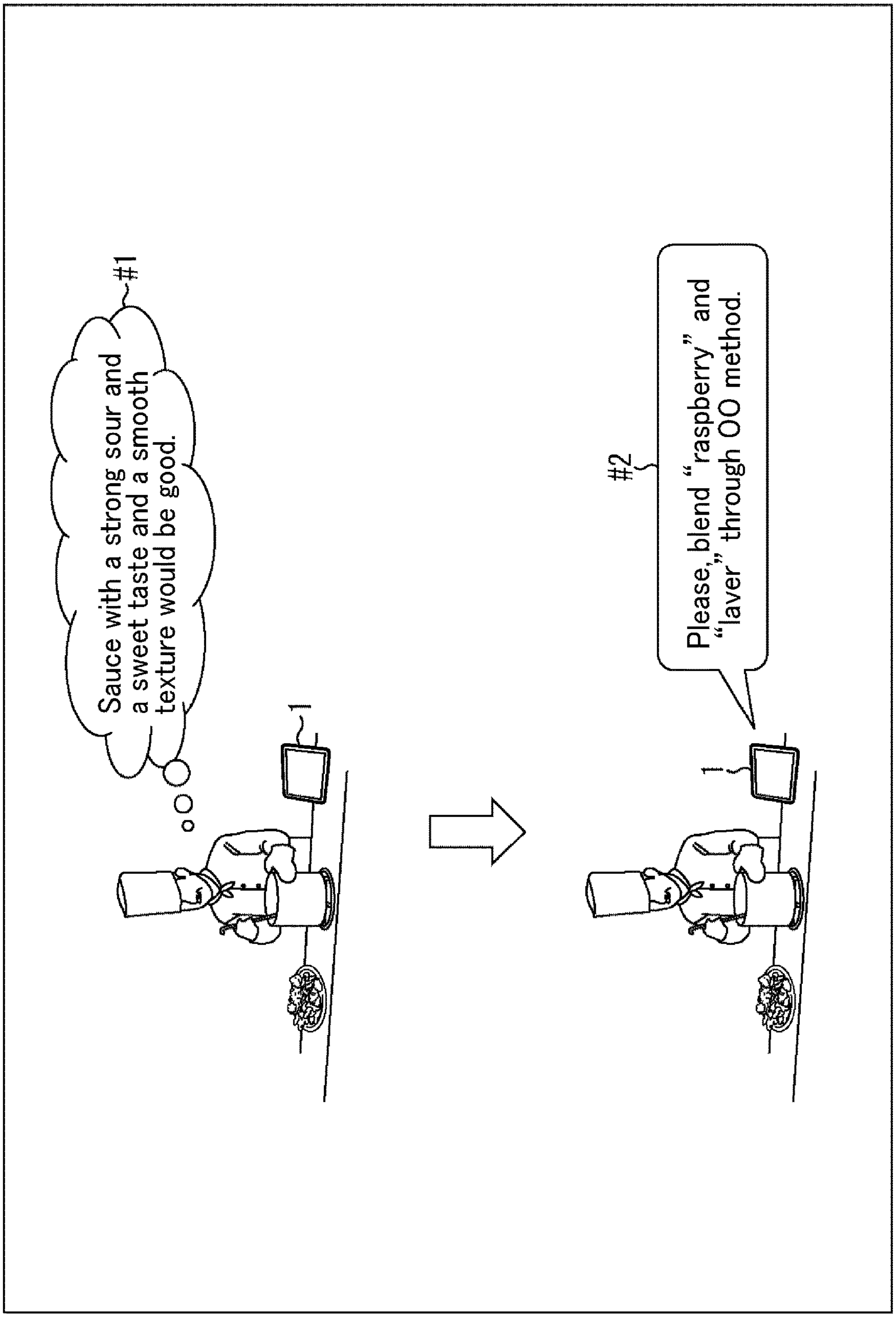
FIG. 1 is a diagram illustrating an example of presentation of a recipe by an information processing device according to an embodiment of the present technology.

FIG. 1 is a diagram illustrating an example of presentation of a recipe by an information processing device according to an embodiment of the present technology.

A situation in which a chef who is cooking is thinking what sauce will be good for a cooked dish is shown in the upper part of FIG. 1. In the example of FIG. 1, an information processing device 1 that is a tablet terminal is placed near the chef. The information processing device 1 has a function of presenting a new recipe in response to a request from a chef.

Meanwhile, a dish means a finished product obtained through cooking. Cooking means a process of making a dish or an action (operation) of making a dish.

For example, it is assumed that a chef wants “a sauce with a strong sweet and sour taste and a smooth texture” as illustrated in balloon #1. In this example, presentation of a recipe is performed according to designation of a flavor such as “strong sweet and sour taste and smooth texture”.

FIG. 2 is a diagram illustrating an example of components of a flavor.

Deliciousness that a person feels in the brain, that is, “flavor” is composed of a combination of taste obtained by the human sense of taste, aromas obtained by the human sense of smell, and texture obtained by the human sense of touch, as illustrated in FIG. 2.

Figure 3:
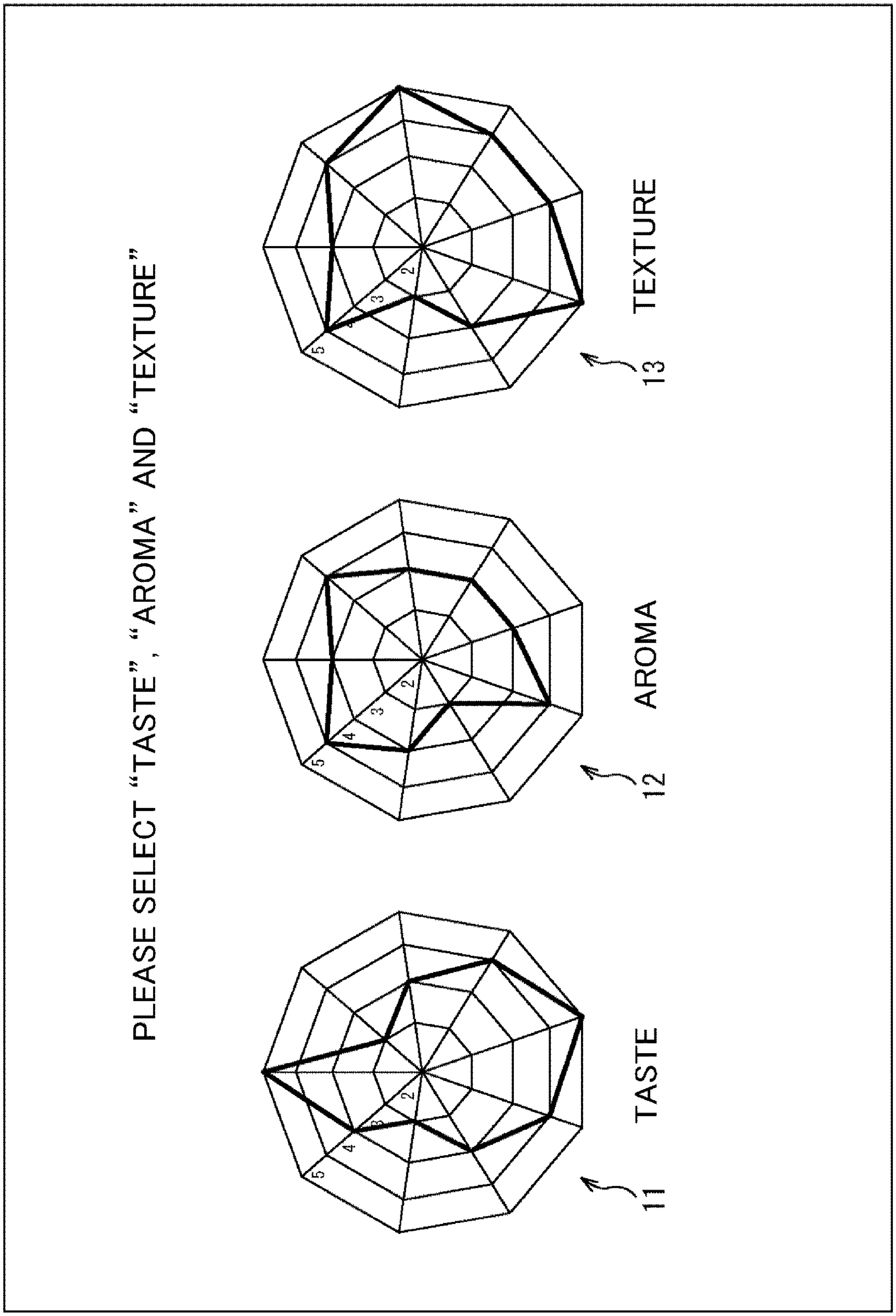
FIG. 3 is a diagram illustrating an example of a screen used to designate a flavor.

FIG. 3 is a diagram illustrating an example of a screen used to designate a flavor.

The flavor designation screen illustrated in FIG. 3 is displayed when a chef performs a predetermined operation on the information processing device 1. In the example of FIG. 3, three radar charts 11 to 13 are displayed. The radar charts 11 to 13 correspond to a radar chart used to designate a flavor, a radar chart used to designate an aroma, and a radar chart used to designate a texture.

For example, the radar chart 11 has axes of nine types of taste elements. Five basic tastes including a salty taste, a sour taste, a bitter taste, a sweet taste, and a delicious taste, and the like are taste elements. For example, a chef may designate a value of each element by touching the position of each element on the radar chart with a finger.

Although each of taste, aroma and texture has nine types of elements in the example of FIG. 3, the numbers of elements thereof may be different.

A flavor may be designated using voice designation instead of using the radar charts as illustrated in FIG. 3. When a flavor is designated using voice designation, voice recognition, language analysis, and the like are performed and the meaning of speech of a chef is identified in the information processing device 1.

A flavor may be designated by directly inputting a value of each element through a keyboard or the like instead of designating a value on a radar chart.

Referring back to FIG. 1, when a sauce flavor desired by the chef is designated as described above, a combination of food ingredients and a cooking process for realizing the flavor desired by the chef are determined in the information processing device 1 and presented to the chef as illustrated in balloon #2. In the example of FIG. 1, the information processing device 1 performs presentation of “Please blend raspberry and layer through ○○ method”.

That is, in this example, a cooking recipe including the sauce is composed of information on food ingredients used for cooking and a cooking process. “Raspberry” and “laver” are information on food ingredients and “blending through ○○ method” is information on a cooking process.

The chef can receive such a presentation made by the information processing device 1 and make a dish according to the presentation or get a hint therefrom and devise a new sauce. The information processing device 1 can also be regarded as a recipe generator that presents a new recipe itself or information that becomes a hint for a new recipe to a chef.

<Generation of Recipe>

Information Used for Generation of Recipe

Figure 4:
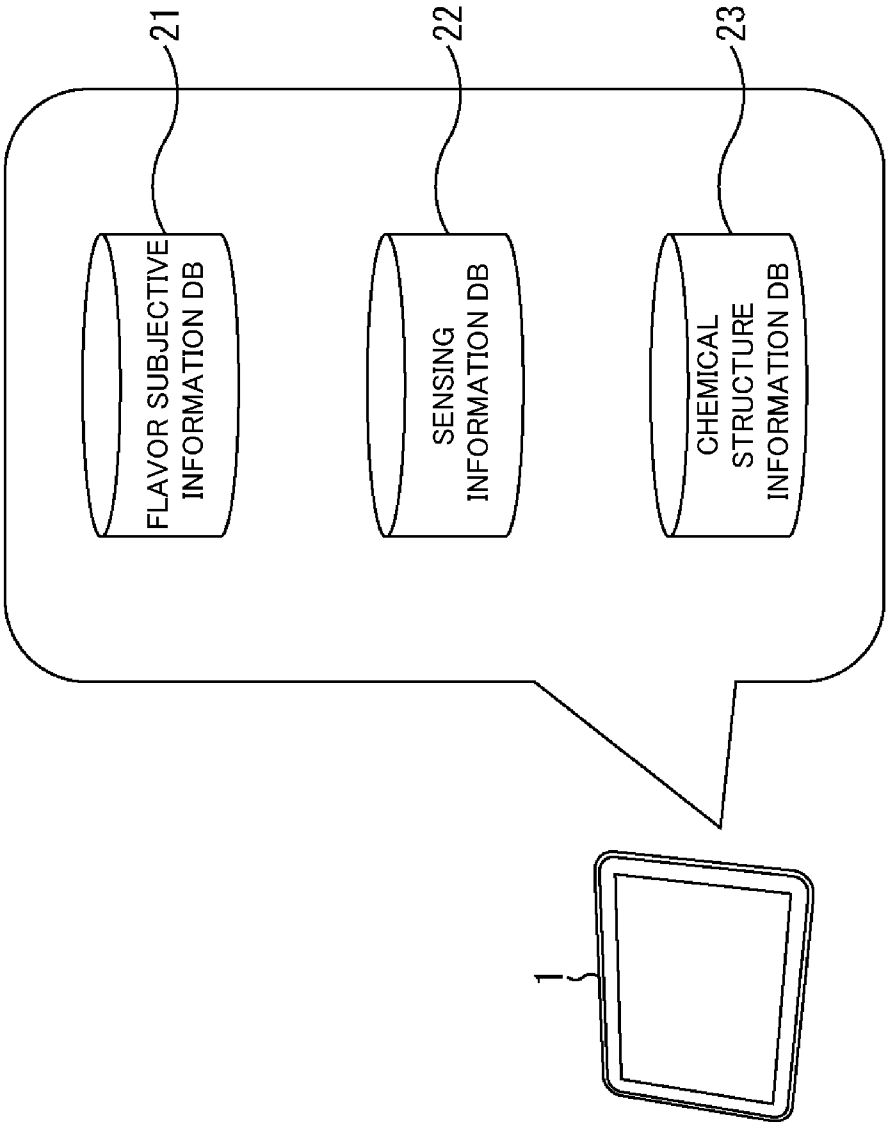
FIG. 4 is a diagram illustrating an example of databases used for generation of a recipe.

FIG. 4 is a diagram illustrating an example of databases used for generation of a recipe.

As illustrated in FIG. 4, the information processing device 1 is provided with a flavor subjective information DB 21, a sensing information DB 22, and a chemical structure information DB 23.

The databases as illustrated in FIG. 4 may be provided in a server on the Internet instead of the information processing device 1. One or two of the three types of databases may be provided in the information processing device 1 and other database may be provided in a server on the Internet.

Figure 5:
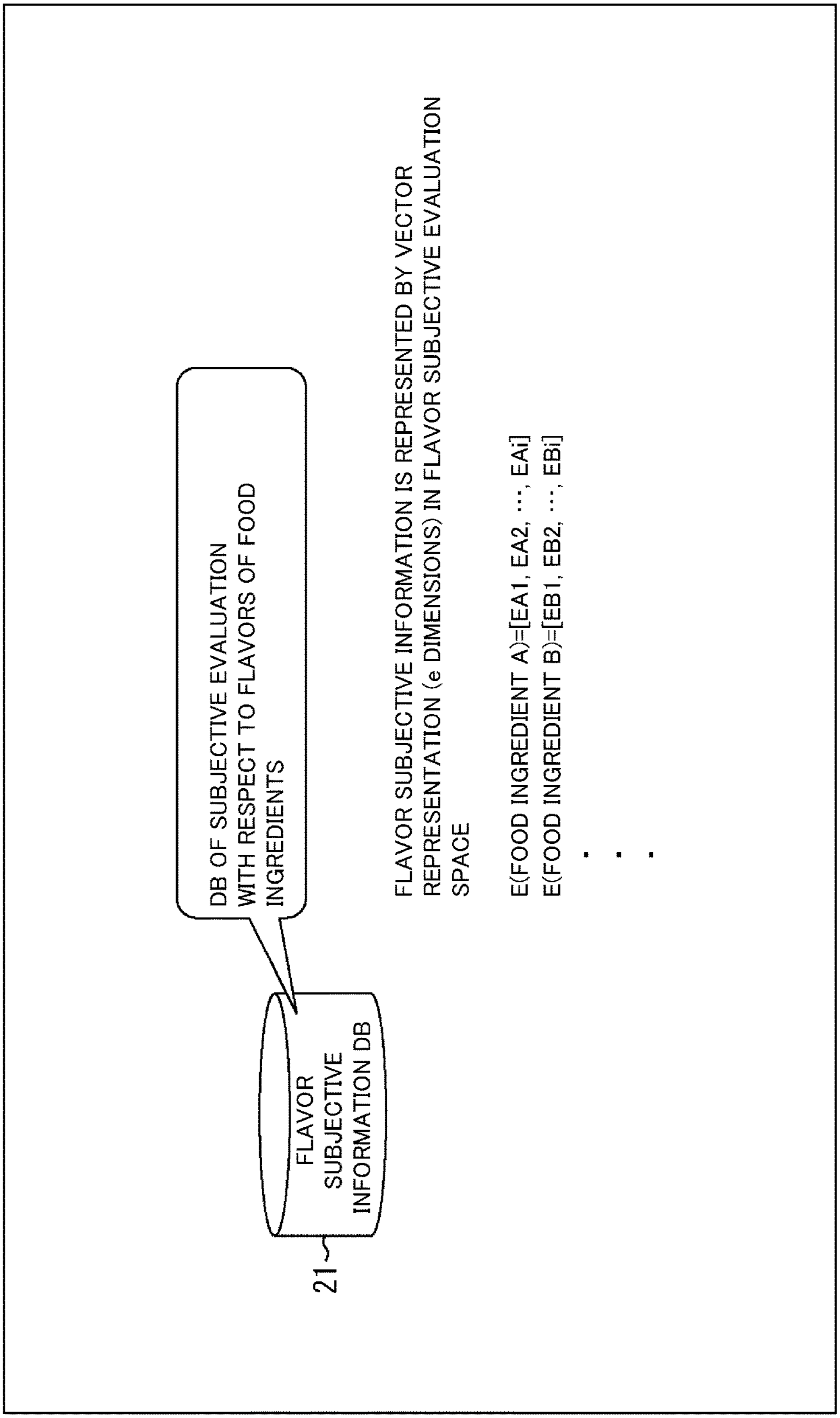
FIG. 5 is a diagram illustrating an example of information stored in a flavor subjective information DB.

FIG. 5 is a diagram illustrating an example of information stored in the flavor subjective information DB 21.

The flavor subjective information DB 21 is a database of subjective evaluation with respect to a flavor of each food ingredient. For example, information representing subjective evaluation values of a flavor on a predetermined scale from a plurality of persons who have eaten each food ingredient is stored as flavor subjective information in the flavor subjective information DB 21.

For example, flavor subjective information on a food ingredient A and a food ingredient B may be represented by vector representation (e dimensions) in a flavor subjective evaluation space E, as represented by the following mathematical formula (1).

[Math. 1]

$$E(\text{Food ingredient } A)=[EA1, EA2, \ldots, EAi]$$

$$E(\text{Food ingredient } B)=[EB1, EB2, \ldots, EBi] \tag{1}$$

Other food ingredients are similarly represented by vectors having each item of subjective evaluation as an element. For example, EAi is a coefficient corresponding to an evaluation value of an item with index i included in subjective evaluation of the food ingredient A.

Figure 6:
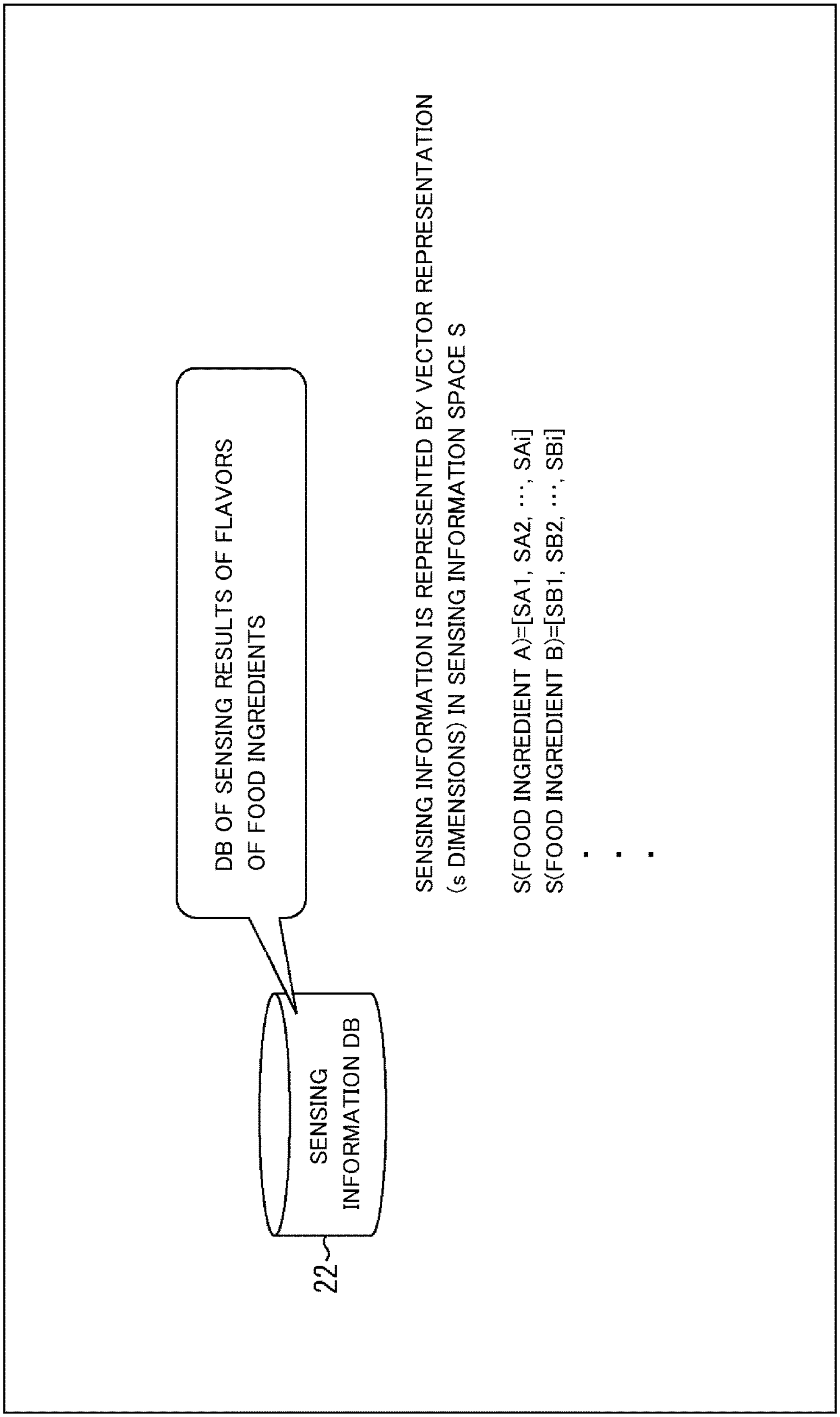
FIG. 6 is a diagram illustrating an example of information stored in a sensing information DB.

FIG. 6 is a diagram illustrating an example of information stored in the sensing information DB 22.

The sensing information DB 22 is a database of a flavor sensing result of each food ingredient. For example, a flavor of each food ingredient is measured by a flavor measuring instrument and sensing information obtained as a measurement result is stored in the sensing information DB 22. Since a flavor is represented by taste, aroma, and texture, as described above, a flavor of each food ingredient is measured using a taste measuring instrument, an aroma measuring instrument, a texture measuring instrument, and the like. Meanwhile, texture includes elasticity, viscosity, temperature, and the like.

Sensing information of food ingredients A and B is represented by vector representation (s dimensions) in a sensing information space S, as represented by the following mathematical formula (2).

[Math. 2]

$$S(\text{Food ingredient } A)=[SA1, SA2, \ldots, SAi]$$

$$S(\text{Food ingredient } B)=[SB1, SB2, \ldots, SBi] \tag{2}$$

Other food ingredients are similarly represented by vectors having each item of sensing information as an element. For example, SAi is a coefficient corresponding to a sensor value of an item with index i included in sensing information of the food ingredient A.

Figure 7:
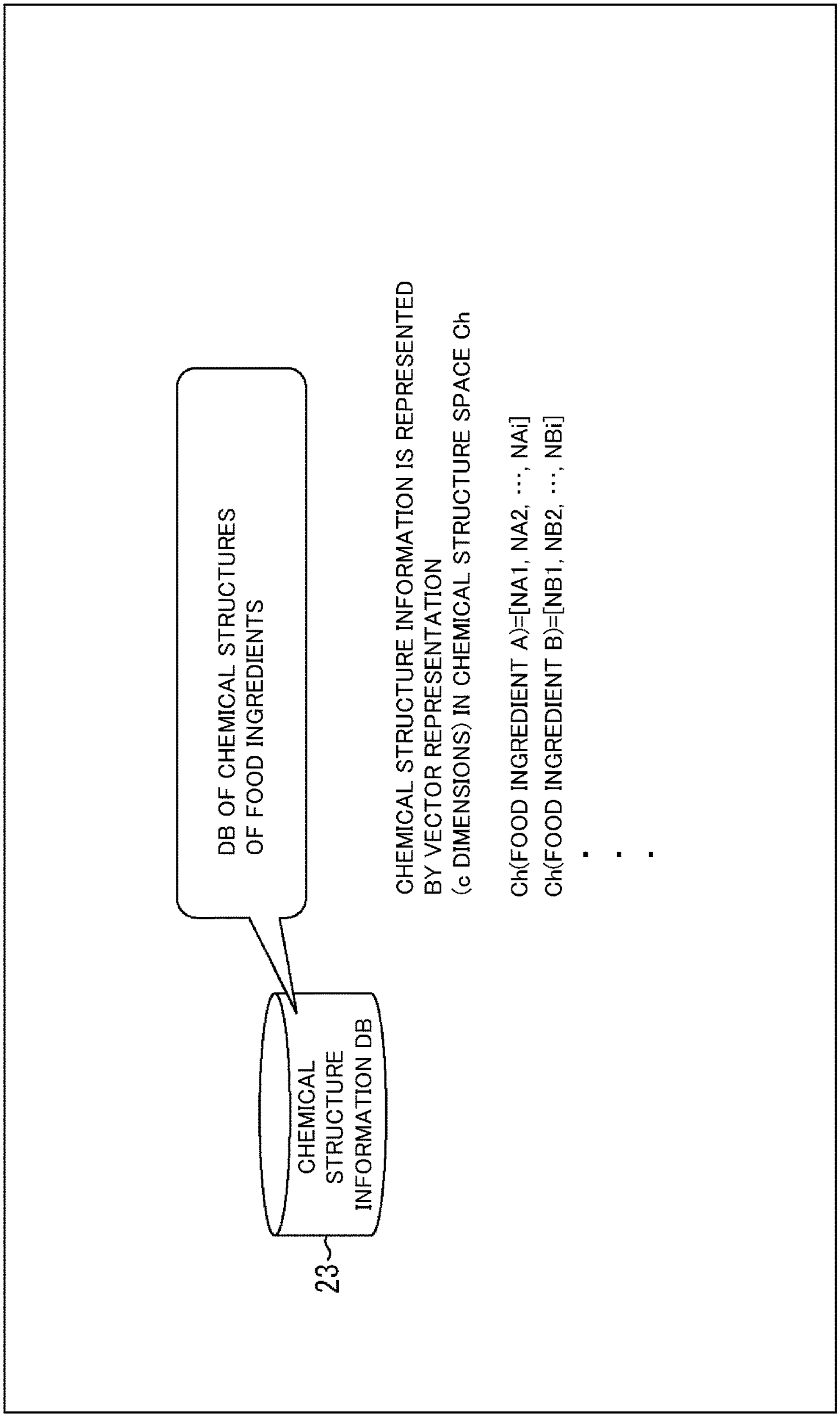
FIG. 7 is a diagram illustrating an example of information stored in a chemical structure information DB.

FIG. 7 is a diagram illustrating an example of information stored in the chemical structure information DB 23.

The chemical structure information DB 23 is a database of chemical structures of food ingredients. For example, a chemical structure of each food ingredient is measured by a separation analyzer using the principle of chromatography and chemical structure information obtained as a measurement result is stored in the chemical structure information DB 23.

Chemical structure information on food ingredients A and B is represented by vector representation (c dimensions) in a chemical structure space Ch using a molecular descriptor, as represented by the following mathematical formula (3).

[Math. 3]

$$Ch(\text{Food ingredient } A)=[NA1, NA2, \ldots, NAi]$$

$$Ch(\text{Food ingredient } B)=[NB1, NB2, \ldots, NBi] \tag{3}$$

Other food ingredients are similarly represented by vectors having chemical substances used to represent a chemical structure as elements. For example, NAi is a coefficient corresponding to the amount of a chemical substance with index i included in the food ingredient A. There may be a chemical substance simply present in each of the food ingredients A and B, and the coefficient of this chemical substance may be assumed to be 0.

Vectorization of a chemical structure is performed using a molecular descriptor in this manner. Vectorization using the molecular descriptor is performed by detecting chemical substances included in a food ingredient and the amounts thereof by a separation analyzer, setting each chemical substance Ck to one element of a c-dimensional vector, and setting the amount (the number of moles, mass, or the like) of a chemical substance Ck included in the food ingredient to Nk. A food ingredient X is represented by the following mathematical formula (4).

[Math. 4]

$$Ch(X)=[N1, \ldots, Nk, \ldots, Nc] \tag{4}$$

The above description is a descriptor according to the number of fragments which is a molecular descriptor. The chemical substance Ck includes —$CH_3$, —OH, —$NH_2$, —COOH, —$CH_2$-, —$CH_2$-$CH_2$-, and the like. The chemical structure of each food ingredient may be represented using other description methods such as a structure descriptor and a count descriptor.

In addition to chemical structures, information representing other chemical features such as properties and reaction may be provided in the chemical structure information DB 23.

Figure 8:
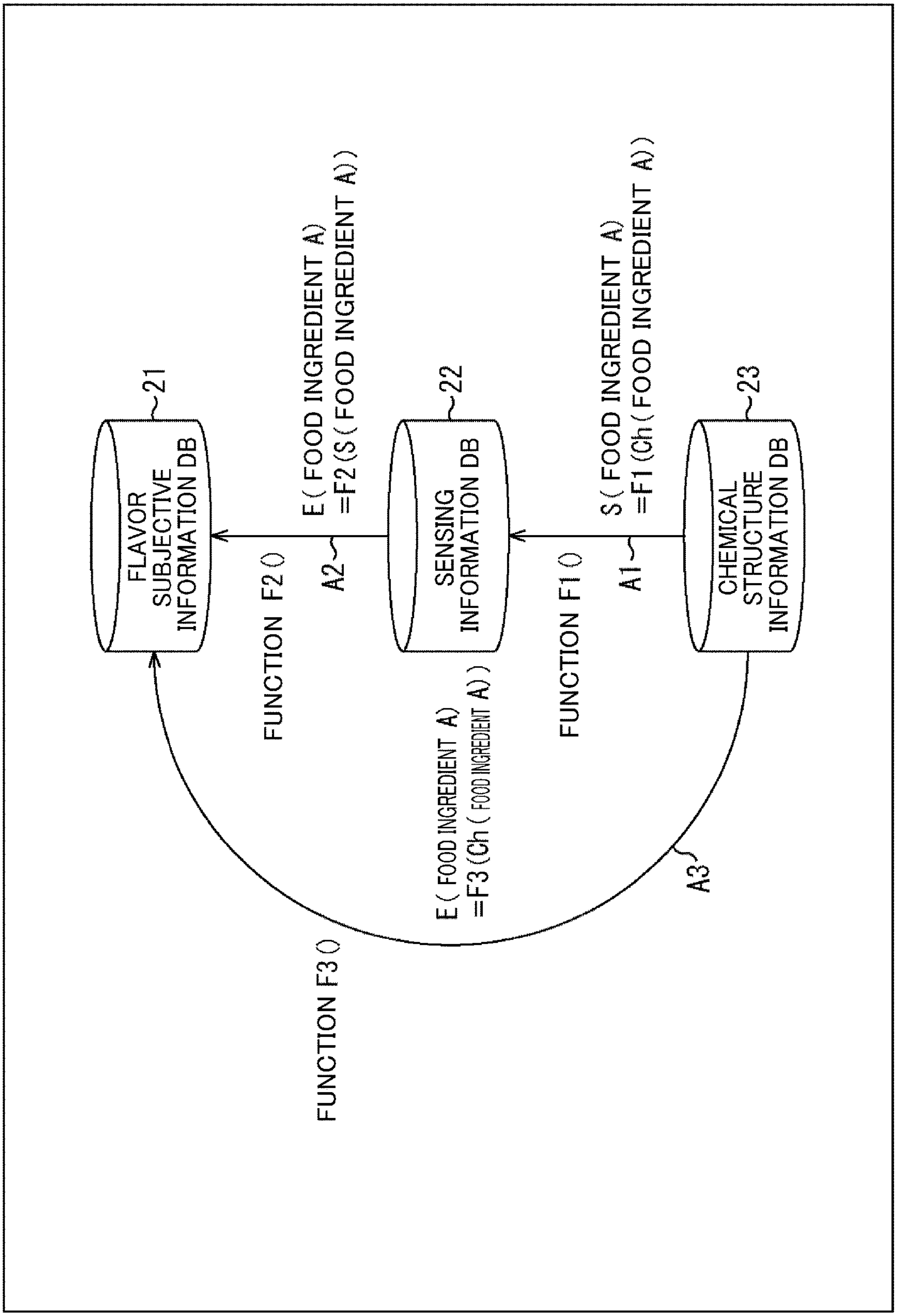
FIG. 8 is a diagram showing relations between databases.

FIG. 8 is a diagram showing relations between databases.

As indicated by arrows A1 to A3, a function used for transformation from a value (vector) of each space into a value of another space is learned according to machine learning such as deep learning.

A function F1 indicated by the arrow A1 is used to transform a value of the chemical structure space Ch into a value of the sensing information space S. A function F2 indicated by the arrow A2 is used to transform a value of the sensing information space S into a value of the flavor subjective evaluation space E. A function F3 indicated by the arrow A3 is used to transform a value of the chemical structure space Ch into a value of the flavor subjective evaluation space E.

For example, the function F1 may be constructed by a neural network (NN) that receives chemical structure information on each food ingredient represented by the above-described vector representation and outputs sensing information of each food ingredient. Learning of the function F1 may be performed, for example, by using chemical structure information on a certain food ingredient as learning data and using sensing information on the same food ingredient as teacher data.

An inverse function of each function is learned according to machine learning such as deep learning.

Figure 9:
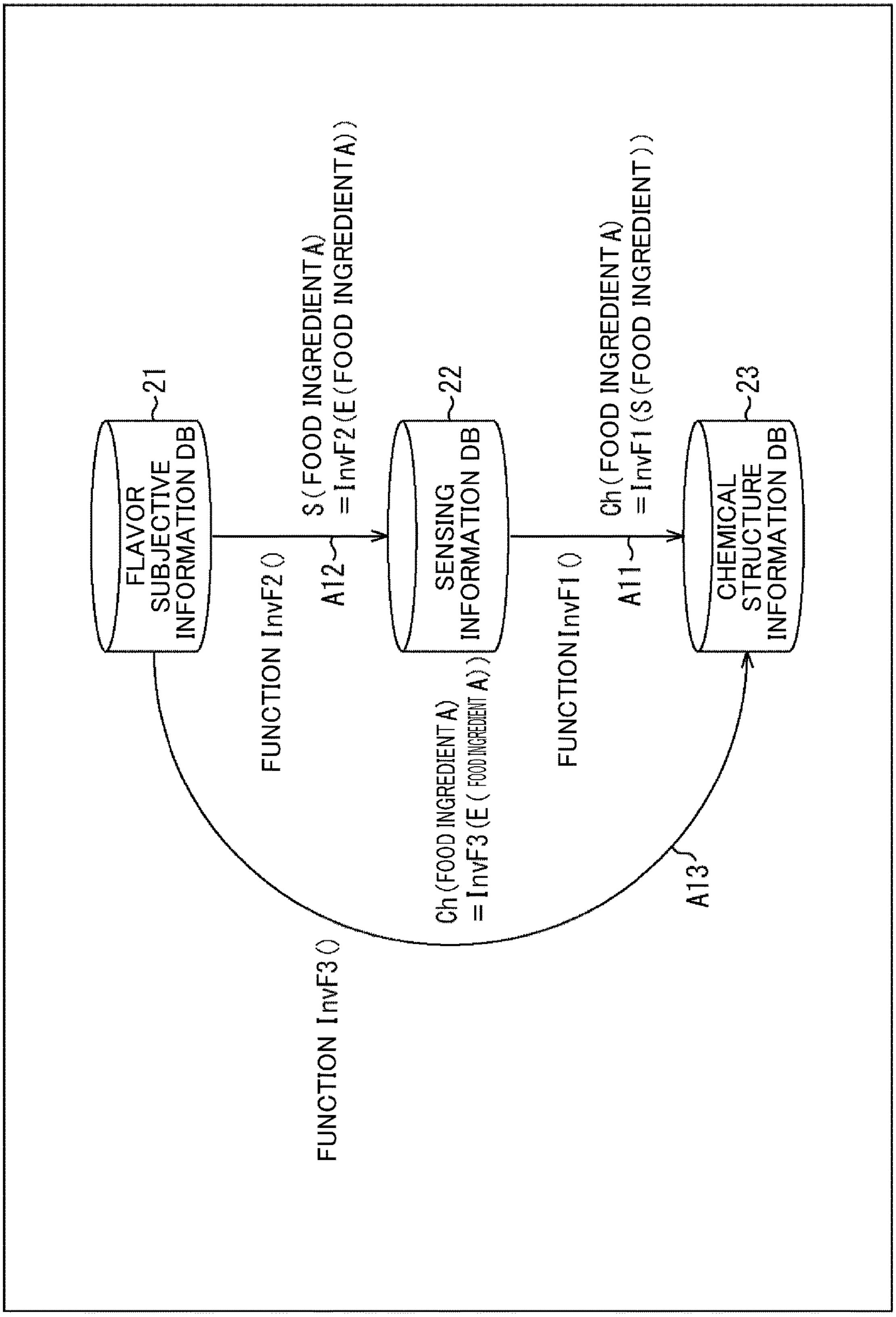
FIG. 9 is a diagram showing relations between databases.

A function InvF1 indicated by an arrow A11 of FIG. 9 is used to transform a value of the sensing information space S into a value of the chemical structure space Ch. A function InvF2 indicated by an arrow A12 is used to transform a value of the flavor subjective evaluation space E into a value of the sensing information space S. A function InvF3 indicated by an arrow A13 is used to transform a value of the flavor subjective evaluation space E into a value of the chemical structure space Ch.

Generation of a new recipe is performed on the basis of the above-described database information and functions representing relations between databases.

Figure 10:
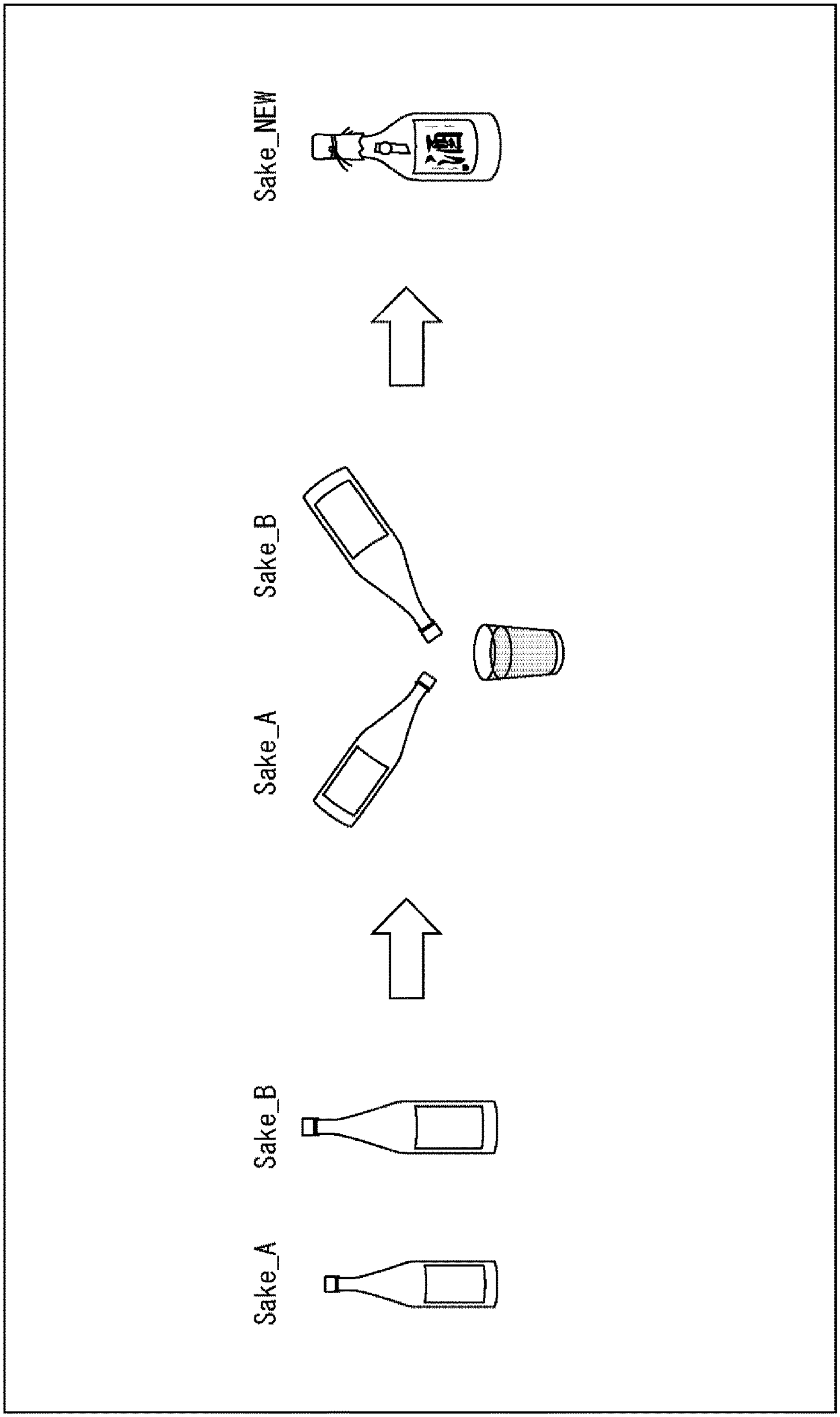
FIG. 10 is a diagram illustrating an example of generating a new recipe.

Specific example of generation of recipe FIG. 10 is a diagram illustrating an example of generating a new recipe.

Here, blending of sake will be described. Blending of sake refers to making sake with a new flavor by blending sake of a plurality of brands.

In the example of FIG. 10, sake Sake_A of a certain brand and sake Sake_B of another brand are blended to create sake Sake_NEW.

Sake brands that are blending targets correspond to food ingredients in cooking, and blending amounts, a temperature, and the like correspond to a cooking process. In the information processing device 1, which brands will be blended and how the brands will be blended are specified and a recipe representing the specified details is generated.

Figure 11:
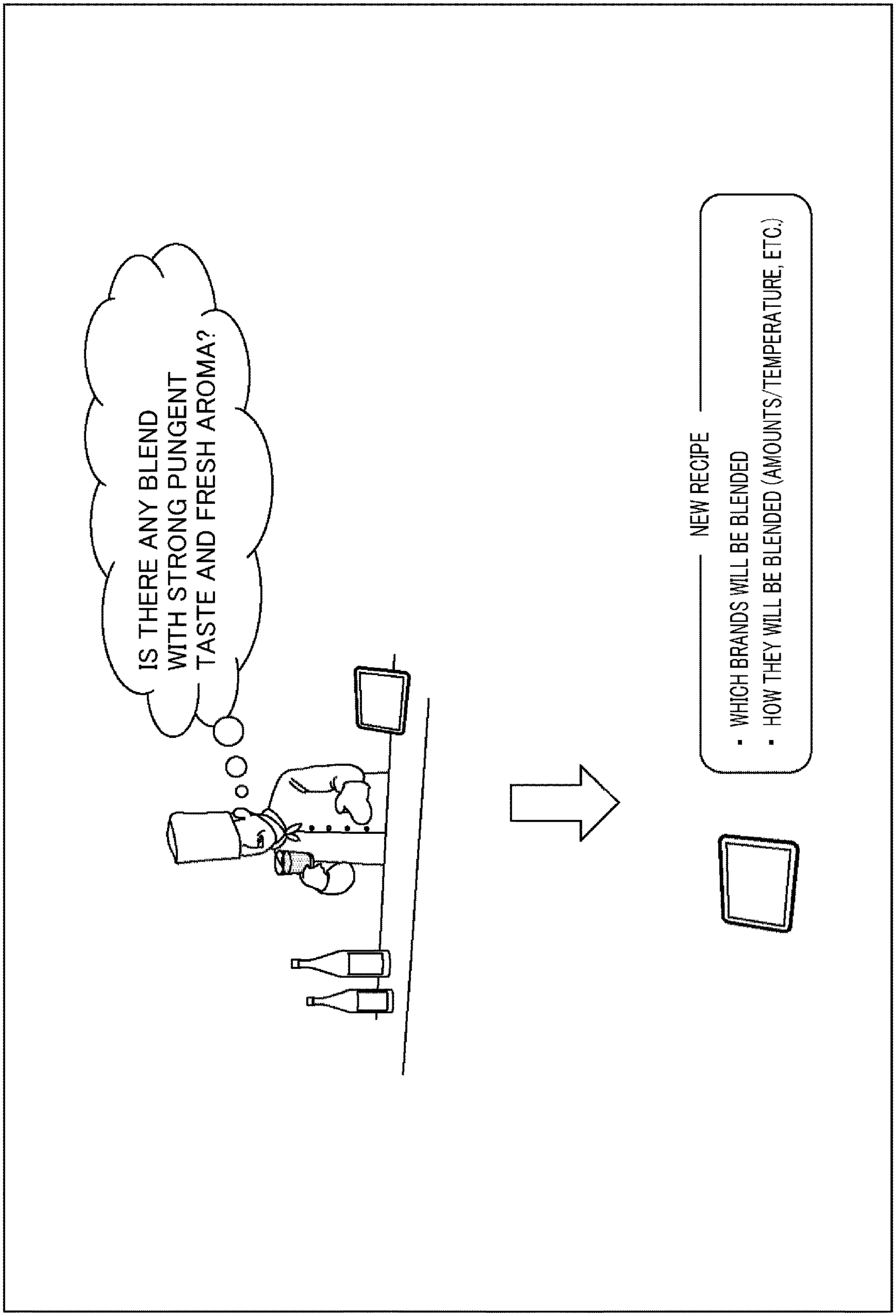
FIG. 11 is a diagram illustrating an example of presentation of a recipe with respect to blending of sake.

FIG. 11 is a diagram illustrating an example of presentation of a recipe with respect to blending of sake.

In blending of sake, a chef requests presentation of a recipe by designating a flavor of sake that he/she wants to make as a condition.

In the example of FIG. 11, presentation of a recipe for making sake with a flavor of "strong pungent taste and fresh aroma" is requested. The flavor of "strong pungent taste and fresh aroma" is designated using the screen as described above with reference to FIG. 3.

In the information processing device 1, a combination of brands for making sake with the flavor of "strong pungent taste and fresh aroma" and how they will be blended are specified and presented to the chef.

Figure 12:
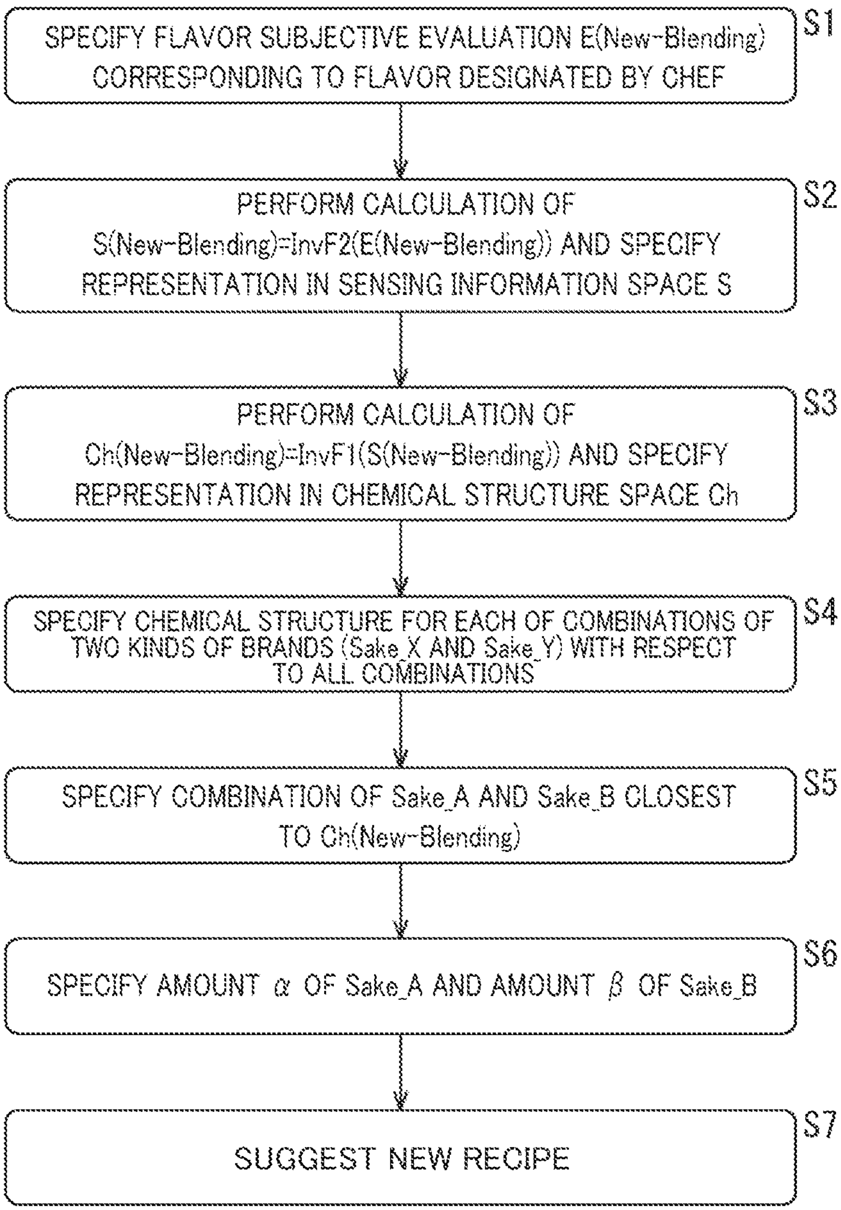
FIG. 12 is a flowchart illustrating a flow of a series of processing for generating a recipe.

FIG. 12 is a flowchart illustrating a flow of a series of processing of generating a recipe with respect to blending of sake.

When the chef designates the flavor of "strong pungent taste and fresh aroma", the information processing device 1 specifies flavor subjective evaluation E(New−Blending) with reference to the flavor subjective information DB 21 in step S1. The flavor subjective evaluation E(New−Blending) is an evaluation value representing the flavor designated by the chef.

Figure 13:
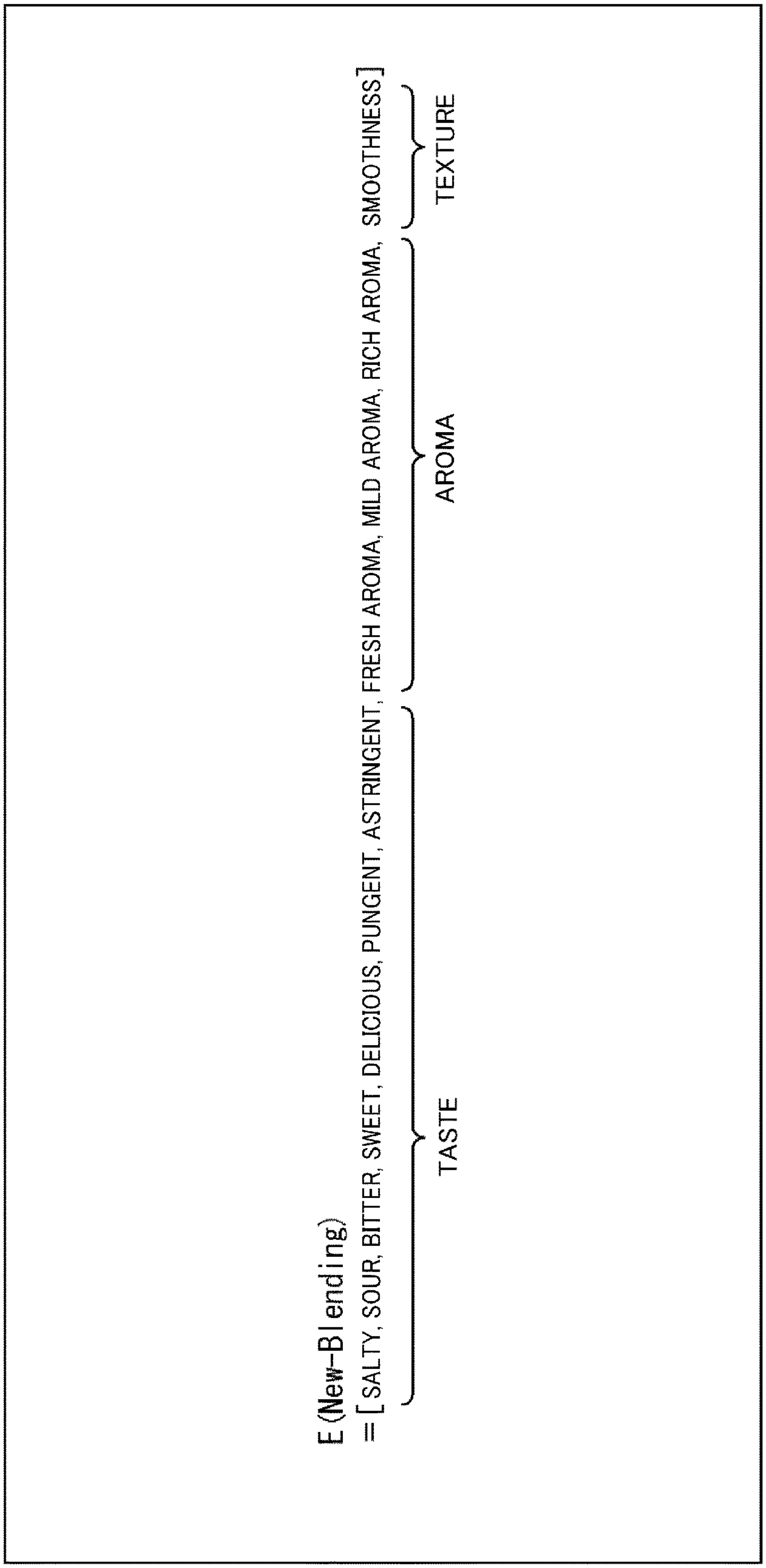
FIG. 13 is a diagram illustrating an example of flavor subjective evaluation.

FIG. 13 is a diagram illustrating an example of the flavor subjective evaluation E(New−Blending).

As illustrated in FIG. 13, the flavor subjective evaluation E(New−Blending) is represented by a vector composed of elements such as a salty taste, a sour taste, a bitter taste, a sweet taste, a delicious taste, a pungent taste, an astringent taste, a fresh aroma, a mild aroma, a rich aroma, smoothness, and the like. A value of each element is a value according to designation by the chef.

Among the elements illustrated in FIG. 13, a salty taste, a sour taste, a bitter taste, a sweet taste, a delicious taste, a pungent taste, and an astringent taste are elements with respect to tastes. A fresh aroma, a mild aroma, and a rich aroma are elements with respect to aromas. Smoothness is an element related to texture.

Using this flavor subjective evaluation E(New−Blending) as a starting point, which brands will be blended and how the brands will be blended are specified.

In step S2 of FIG. 12, the information processing device 1 specifies a value of the sensing information space S corresponding to the flavor subjective evaluation E(New−Blending). The value S(New−Blending) of the sensing information space S is obtained according to the following mathematical formula (5).

[Math. 5]

$$S(\text{New−Blending})=\text{Inv}F2(E(\text{New−Blending})) \quad (5)$$

As described above, the function InvF2 (FIG. 9) is a function used when a value of the flavor subjective evaluation space E is transformed into a value of the sensing information space S.

In step S3, the information processing device 1 specifies a value of the chemical structure space Ch corresponding to the sensing information S(New−Blending). The value Ch(New−Blending) of the chemical structure space Ch are obtained according to the following mathematical formula (6).

[Math. 6]

$$Ch(\text{New−Blending})=\text{Inv}F1(S(\text{New−Blending})) \quad (6)$$

As described above, the function InvF1 is a function used when a value of the sensing information space S is transformed into a value of the chemical structure space Ch.

Accordingly, a chemical structure of sake for realizing the flavor designated by the chef is specified.

In step S4, the information processing device 1 selects combinations of all brands having chemical structure information stored in the chemical structure information DB 23 and specifies a chemical structure of each combination on the basis of the chemical structure information.

Here, sake Sake_X and sake Sake_Y are adopted as two kinds of brands, all combinations of the brands are selected, and a chemical structure of each combination is specified. Combinations of three or more kinds of brands as well as two kinds of brands may be selected.

In step S5, the information processing device 1 specifies a combination of sake Sake_A and sake Sake_B having a chemical structure closest to the value of the chemical structure Ch(New−Blending) for realizing the flavor designated by the chef from all the combinations.

For example, a combination of sake Sake_A and sake Sake_B is specified on the basis of a distance in the chemical structure space Ch. The combination of sake Sake_A and sake Sake_B specified here is a combination having a closest distance to Ch(New−Blending) in the chemical structure space Ch.

In step S6, the information processing device 1 specifies an amount α of sake Sake_A and an amount ß of sake Sake_B. A brand for realizing the flavor designated by the chef is represented by the following mathematical formula (7).

[Math. 7]

$$Ch(\text{New-Blending})=\alpha\times Ch(\text{Sake\_}A)+\beta\times Ch(\text{Sake\_}B) \quad (7)$$

α and β are obtained as follows. Here, it is assumed that A=Ch(Sake_A), B=Ch(Sake_B), C=Ch(New-Blending) using a matrix representing the chemical structure for brief description. It is assumed that $A^t$=Ch(Sake_A)$^t$, $B^t$=Ch (Sake_B)$^t$, $C^t$=Ch(New-Blending)$^t$. The superscript t represents transposition.

The above mathematical formula (7) is represented as the following mathematical formula (8).

[Math. 8]

$$C=\alpha A+\beta B \quad (8)$$

The above mathematical formula (8) is represented as the following mathematical formula (9).

[Math. 9]

$$\alpha AA^t=(C-\beta B)A^t \quad (9)$$

α is obtained according to mathematical formula (10) from mathematical formula (9).

[Math. 10]

$$\alpha=(C-\beta B)A^t(AA^t)^{-1} \quad (10)$$

In the same manner, the amount ß is obtained.

Figure 14:
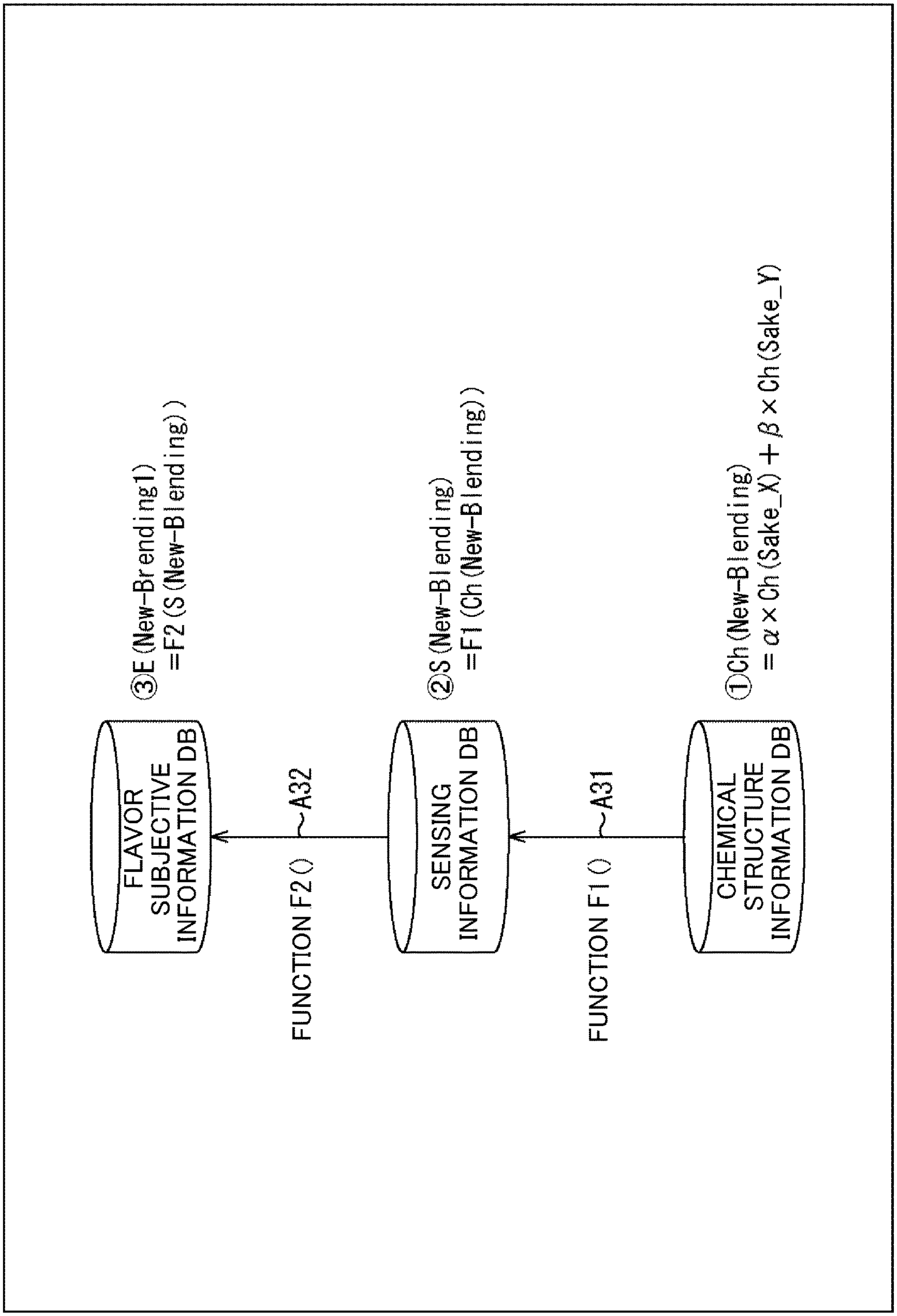
FIG. 14 is a diagram illustrating an example of inverse transformation.

FIG. 14 is a diagram illustrating an example of inverse transformation.

After the combination of sake Sake_A and sake Sake_B and the values α and ß are specified as described above, adjustments are appropriately performed according to inverse transformation.

As indicated by an arrow A31 of FIG. 14, the information processing device 1 specifies a value of the sensing information space S corresponding to the value Ch(New-Blending) of the chemical structure space Ch. The value S(New-Blending) of the sensing information space S is obtained according to the following mathematical formula (11).

[Math. 11]

$$S(\text{New-Blending})=F1(Ch(\text{New-Blending})) \quad (11)$$

In addition, the information processing device 1 specifies a value of the flavor subjective evaluation space E corresponding to the value S(New-Blending) of the sensing information space S. The value E(New-Blending1) of the flavor subjective evaluation space E is obtained according to the following mathematical formula (12).

[Math. 12]

$$E(\text{New-Blending1})=F2(S(\text{New-Blending})) \quad (12)$$

An error ΔE between the flavor subjective evaluation value E(New-Blending) designated by the chef and the flavor subjective evaluation value E(New-Blending1) obtained according to inverse transformation is represented by the following mathematical formula (13).

[Math. 13]

$$\Delta E=E(\text{New-Blending1})-E(\text{New-Blending}) \quad (13)$$

For example, when the error ΔE is less than a threshold value, selection of the combination of brands and selection of the blending amounts α and ß end.

On the other hand, when the error ΔE is greater than the threshold value, the combination of brands and the blending amounts α and ß are adjusted.

In step S7 of FIG. 12, the information processing device 1 presents information including using of sake Sake_A and sake Sake_B and blending of the amount α of sake Sake_A and the amount ß of sake Sake_B to the chef as a new recipe.

Other cooking recipes as well as a recipe with respect to blending of sake are generated through the same processing and presented to a chef.

In this manner, the information processing device 1 presents a recipe by generating a recipe depending on a flavor designated by a chef on each occasion instead of selecting a recipe that meets conditions from a plurality of recipes prepared in advance.

According to the above-described processing, it is possible to generate a cooking recipe depending on a flavor designated by a chef on the basis of relations between flavor subjective information, sensing information, and chemical structure information and to present the recipe.

Flavor subjective information, sensing information, and chemical structure information on sake made by actually blending brands instead of information on each food ingredient (brand) may be measured and learning of relations therebetween may be performed.

At this time, it is possible to easily specify the amounts α and ß depending on a flavor designated by a chef by changing the amounts α and ß and performing learning. For example, learning may be performed by changing a ratio ß/α of the amount ß to the amount α on the basis of the amount α.

In selection of a combination of food ingredients, restrictions for selecting a combination of food ingredients having chemical structures forming a dominant aroma may be imposed. In the case of the above-described example, a brand having a chemical structure similar to the chemical structure that characterizes the taste, aroma, and texture of sake Sake_A is selected as sake Sake_B and a combination of sake Sake_A and sake Sake_B is selected. Such recommendation based on a dominant aroma may be performed by an AI system.

Another Example of Generation of Recipe

Although selection of a combination of sake Sake_A and sake Sake_B is performed by selecting a combination having a chemical structure closest to Ch(New-Blending) in step S5 of FIG. 12, the selection may be performed according to the following method.

First, a brand having a chemical structure closest to Ch(New-Blending) is selected. The selected brand is assumed to be sake Sake_A.

Next, the amounts α and ß when another brand is selected as sake Sake_B are obtained as described above. Values of the chemical structure space Ch of sake Sake_A and sake Sake_B when they have been blended are represented as the above mathematical formula (7).

In the chemical structure space Ch, a combination of sake Sake_A and sake Sake_B closest to Ch(New-Blending) is selected from all combinations.

That is, in this example, sake Sake_B combined with sake Sake_A is selected on the basis of sake Sake_A corresponding to one food ingredient.

A brand having a chemical structure represented by a vector parallel to Ch(New-Blending) in the chemical structure space Ch may be selected as sake Sake_A instead of a brand having a chemical structure closest to Ch(New-Blending).

For example, scalar products of the vector representing Ch(New-Blending) and vectors representing chemical structures of sake Sake_A are divided by normal ||Ch|| and ||A|| and sake Sake_A corresponding to largest ||A|| is selected.

Accordingly, it may be possible to create a recipe using an unexpected food ingredient while realizing a flavor designated by a chef.

<Configuration and Operation of Each Device>

Configuration of Information Processing Device 1

Figure 15:
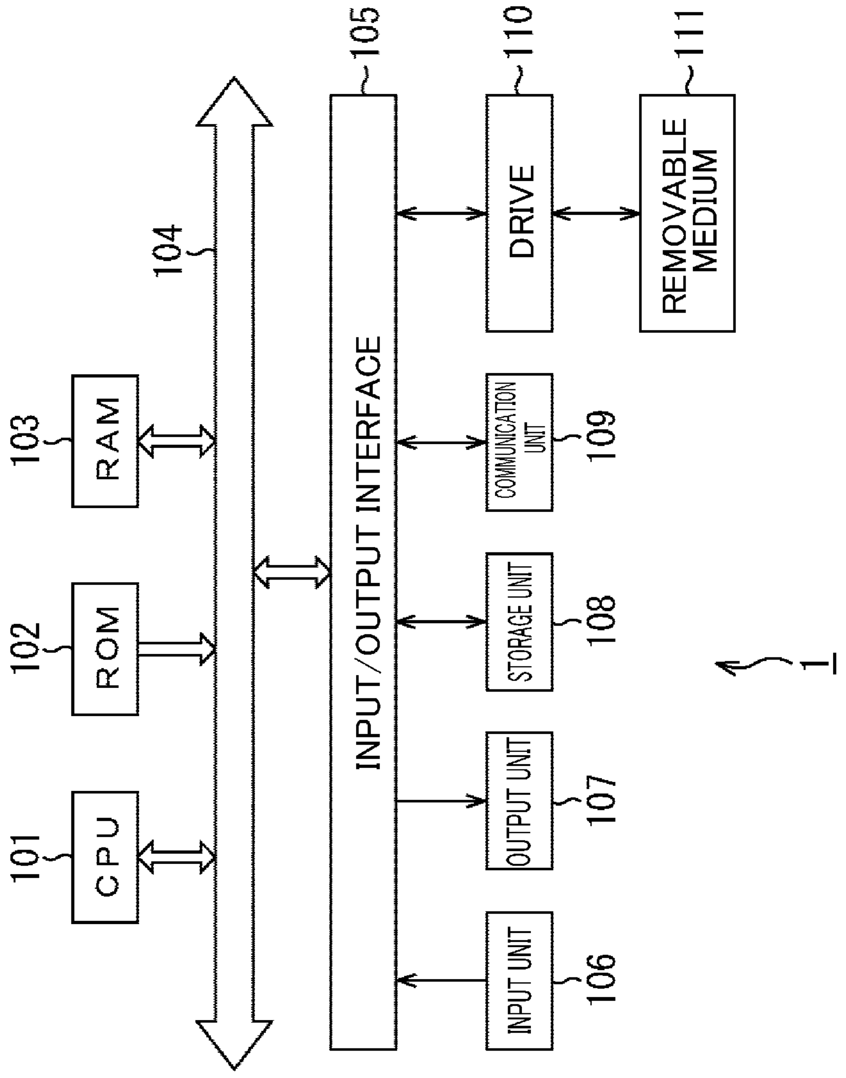
FIG. 15 is a block diagram illustrating a configuration example of hardware of an information processing device.

FIG. 15 is a block diagram illustrating a configuration example of hardware of the information processing device 1.

As illustrated in FIG. 15, the information processing device 1 is configured as a computer such as a tablet terminal. A central processing unit (CPU) 101, a read-only memory (ROM) 102, and a random access memory (RAM) 103 are connected via a bus 104.

An input/output interface 105 is additionally connected to the bus 104. An input unit 106 including a keyboard, a mouse, and the like, and an output unit 107 including a display, a speaker, and the like are connected to the input/output interface 105.

A storage unit 108 including a hard disk or a nonvolatile memory, a communication unit 109 including a network interface, a drive 110 driving a removable medium 111 are connected to the input/output interface 105.

Various types of processing such as generation of a recipe is performed by the CPU 101 loading a program stored in the storage unit 108 to the RAM 103 via the input/output interface 105 and the bus 104 and executing the program.

Figure 16:
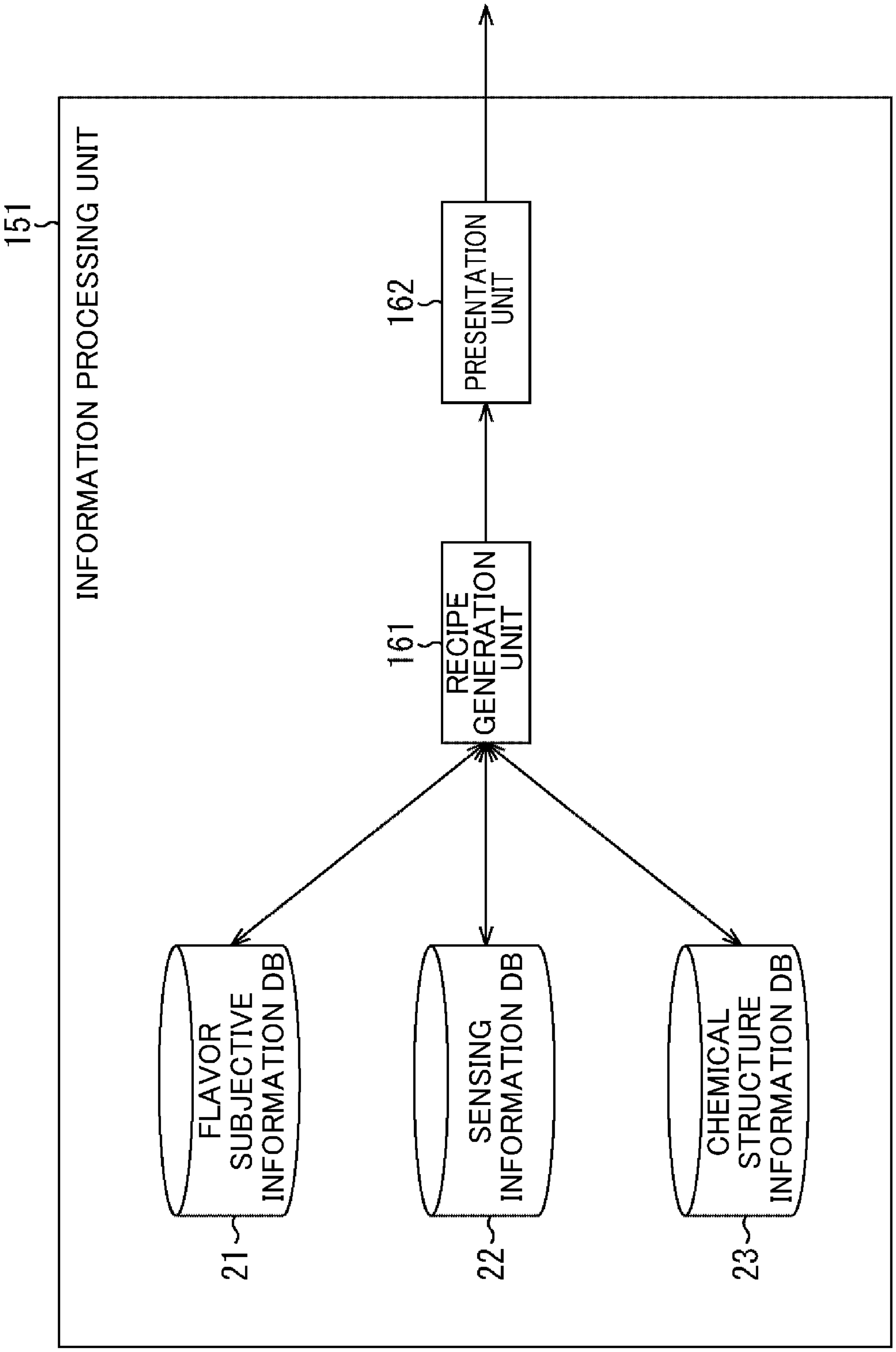
FIG. 16 is a block diagram illustrating a functional configuration example of the information processing device.

FIG. 16 is a block diagram illustrating a functional configuration example of the information processing device 1.

At least some functional units illustrated in FIG. 16 are realized by causing the CPU 101 of FIG. 15 to execute a predetermined program. The same components among the components illustrated in FIG. 16 as those described above are denoted by the same numerals.

As illustrated in FIG. 16, an information processing unit 151 is realized in the information processing device 1. The information processing unit 151 includes a recipe generation unit 161 and a presentation unit 162. The flavor subjective information DB 21, the sensing information DB 22, and the chemical structure information DB 23 are provided in the information processing unit 151.

The recipe generation unit 161 generates a recipe as described above on the basis of information stored in the flavor subjective information DB 21, the sensing information DB 22, and the chemical structure information DB 23 and information representing relations between information when a chef designates a flavor. Information representing a recipe generated by the recipe generation unit 161 is supplied to the presentation unit 162.

Conditions such as a name of a dish, a genre of a dish, a style of a dish such as a Japanese style or an American style, and a food ingredient to be used as well as a flavor may be designated by a chef. In this case, a recipe that meets a condition designated by a chef is generated.

For example, when a food ingredient to be used is designated as a condition, another ingredient to be used in combination with a food ingredient designated by a chef is selected on the basis of the food ingredient and a recipe is generated.

With respect to a recipe generated by the recipe generation unit 161, flavor subjective information, sensing information, and chemical structure information on food ingredients to be used for the recipe may be associated. At the time of presentation of a recipe, flavor subjective information, sensing information, chemical structure information, and the like on food ingredients are presented altogether and thus a chef can create a recipe with reference to the information.

The presentation unit 162 presents the recipe generated by the recipe generation unit 161 to the chef. Presentation of the recipe may be performed through voice using a speaker or performed according to screen display using a display. For example, the presentation unit 162 sequentially presents descriptions of cooking processes of the recipe to the chef.

A series of processing described with reference to FIG. 12 is performed according to the information processing unit 151 having the above-described configuration. Processing of steps S1 to S6 of FIG. 12 corresponds to processing of the recipe generation unit 161 and processing of step S7 corresponds to processing of the presentation unit 162.

Figure 17:
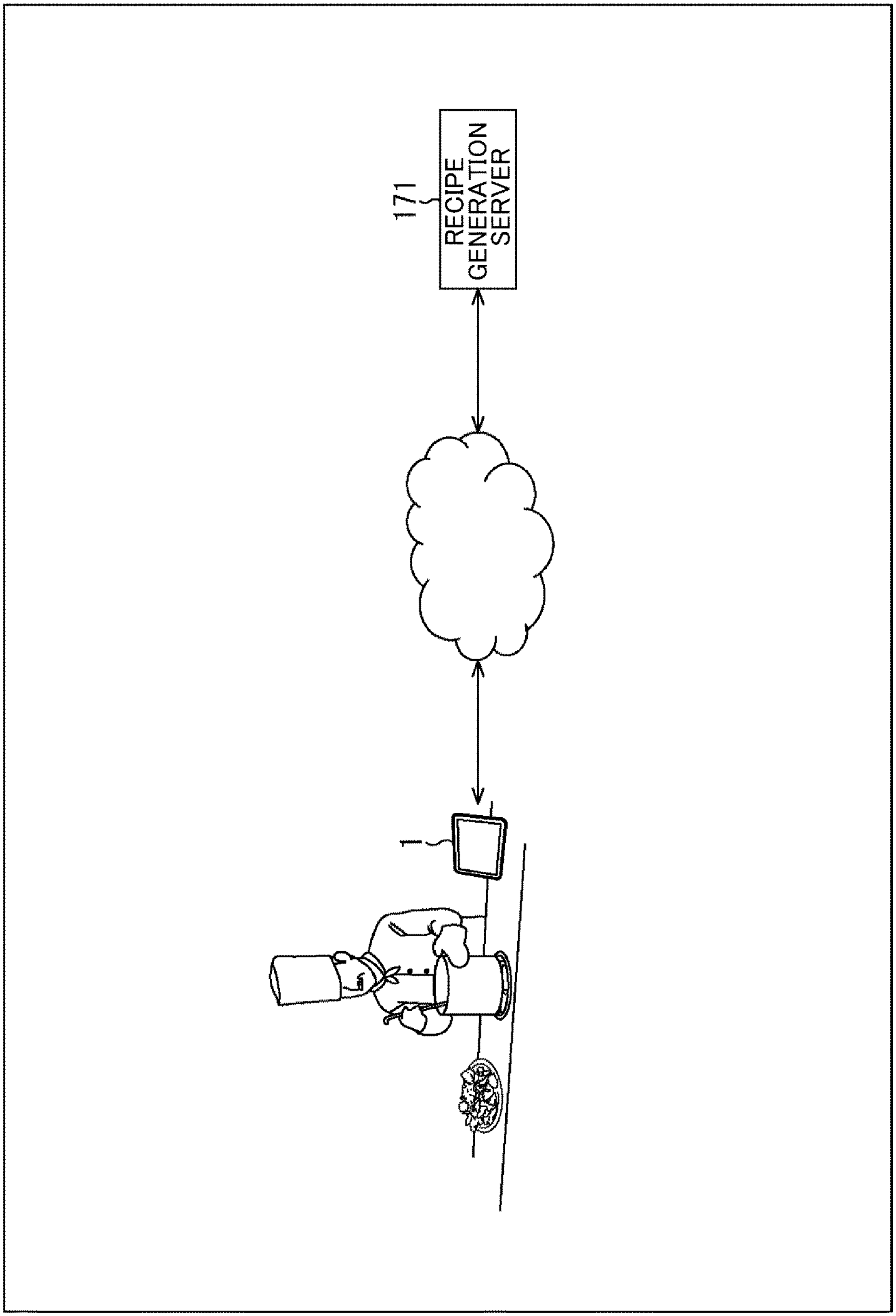
FIG. 17 is a diagram illustrating a configuration example of a network system.

FIG. 17 is a diagram illustrating a configuration example of a network system.

FIG. 17 illustrates a configuration when generation of a new recipe is performed in a recipe generation server 171 on the Internet. The recipe generation server 171 has the same configuration as that of the information processing unit 151 illustrated in FIG. 16.

Communication is performed between the recipe generation server 171 and the information processing device 1 provided on a chef through the Internet. Information representing a flavor or the like designated by the chef is transmitted from the information processing device 1 to the recipe generation server 171.

The recipe generation unit 161 of the recipe generation server 171 receives the information on the flavor designated by the chef, transmitted from the information processing device 1, and generates a recipe.

The presentation unit 162 transmits information on the recipe generated by the recipe generation unit 161 to the information processing device 1 and causes the information processing device 1 to represent the information to the chef.

In this manner, a new recipe can be generated in the recipe generation server 171 on the Internet.

<Example of Control of Cooking Robot>

Configuration of Control System

Although generation of a recipe for a human chef has been described above, a recipe may be generated for a cooking robot. In this case, cooking according to a newly generated recipe is performed by the cooking robot.

Figure 18:
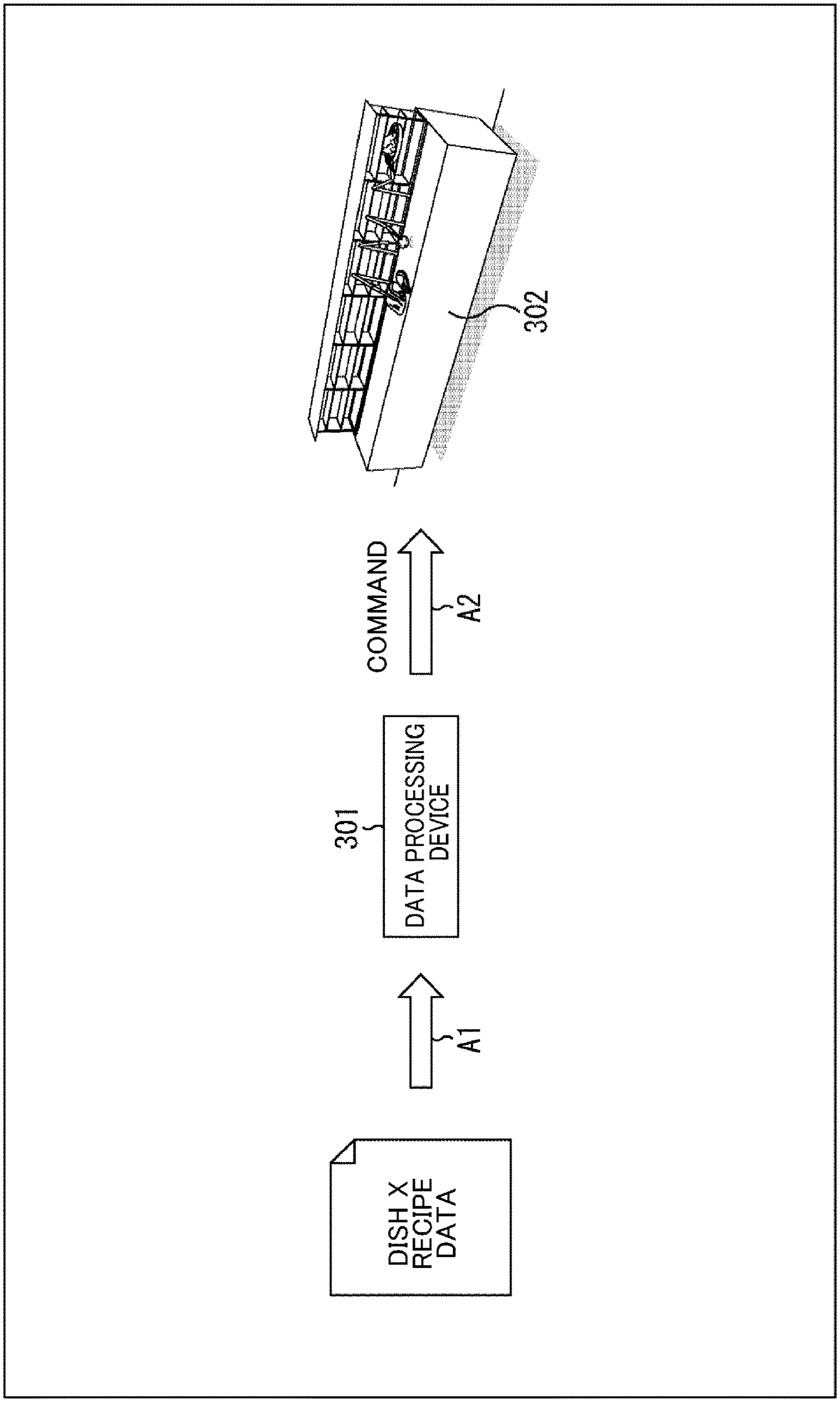
FIG. 18 is a diagram illustrating a configuration example of a control system.

FIG. 18 is a diagram illustrating a configuration example of a control system.

As illustrated in FIG. 18, the control system includes a data processing device 301 and a cooking robot 302. The cooking robot 302 includes a device of a driving system such as a cooking arm and various sensors and has a function of performing cooking. The cooking robot 302 is installed, for example, in a home.

The data processing device 301 controls the cooking robot 302. The data processing device 301 is configured as a computer or the like.

As illustrated in the left part of FIG. 18, the data processing device 301 controls the cooking robot 302 on the basis of recipe data prepared for each dish. Information about each cooking process is described in the recipe data.

The data processing device 301 controls the cooking robot 302 on the basis of the recipe data to cause the cooking robot 302 to make a dish. Data of a recipe generated by the information processing unit 151 of FIG. 16 is supplied to the data processing device 301 and used to control the cooking robot 302.

For example, when recipe data is input as indicated by an arrow A1, the data processing device 301 outputs a command on the basis of description of the recipe data to control a cooking operation of the cooking robot 302, as indicated by an arrow A2.

The cooking robot 302 drives each part such as the cooking arm according to the command supplied from the data processing device 301 and performs a cooking operation of each cooking process. The command includes information for controlling a torque, a driving direction, and a driving amount of a motor provided in the cooking arm, and the like.

Commands are sequentially output from the data processing device 301 to the cooking robot 302 until the dish is completed. The cooking robot 302 performs operations according to commands to finally complete the dish.

Figure 19:
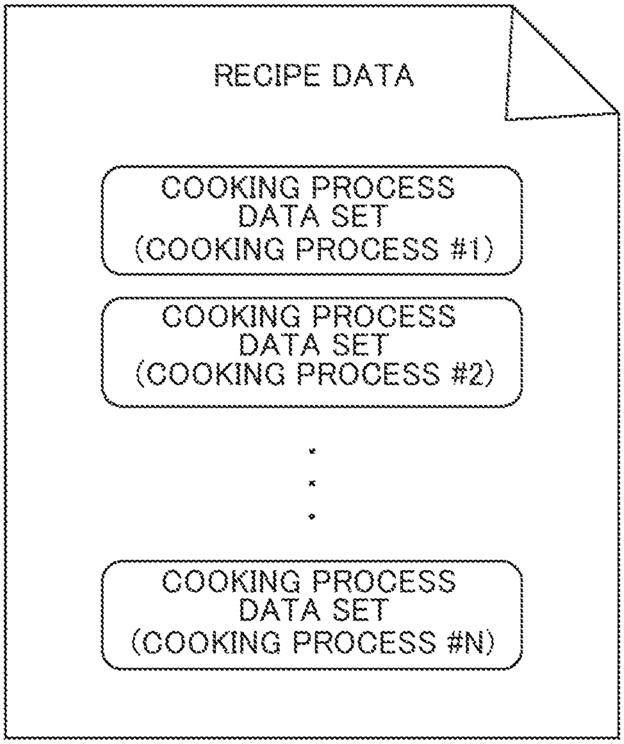
FIG. 19 is a diagram illustrating an example of description of recipe data.

FIG. 19 is a diagram illustrating an example of description of recipe data.

As illustrated in FIG. 19, one piece of recipe data includes a plurality of cooking process data sets. In the example of FIG. 19, a cooking process data set with respect to cooking process #1, a cooking process data set with respect to cooking process #2, . . . , a cooking process data set with respect to cooking process #N are included.

Each cooking process data set includes cooking operation information about a cooking operation for realizing a cooking process. For example, one cooking process data set may be composed of time-series data of cooking operation information for realizing one cooking process.

Cooking operation information includes food ingredient information and operation information.

Food ingredient information is information about food ingredients used in a cooking process. Information about food ingredients includes information representing kinds of the food ingredients, amounts of the food ingredients, sizes of the food ingredients, and the like.

Meanwhile, food ingredients include not only food ingredients that are not cooked but also processed (preprocessed) food ingredients obtained by performing cooking to some degree. Food ingredient information included in cooking operation information of a certain cooking process includes information on food ingredients that have passed through cooking processes before the cooking process.

Operation information is information about a motion of the cooking arm or the like in a cooking process. Information about a motion includes information representing kinds of cooking tools used for cooking, and the like.

For example, operation information of a cooking process of cutting a certain food ingredient may include information representing use of a kitchen knife as a cooking tool and information representing a cutting position, the number of times of cutting, and an acceleration/deceleration, an angle, a speed, and the like of cutting, and the like.

In addition, operation information of a cooking process of stirring liquid food ingredients put into a pot includes information representing use of a spoon as a cooking tool and information representing an acceleration/deceleration, an angle, a speed, a time, and the like of stirring.

Operation information of a cooking process of baking a certain food ingredient using an oven includes information representing use of the oven as a cooking tool and information representing heating power, a baking time, and the like of the oven.

Operation information of a cooking process of dishing up includes information on dishing up representing tableware used for dishing up, arrangement of food ingredients, color tones of food ingredients, and the like.

Figure 20:
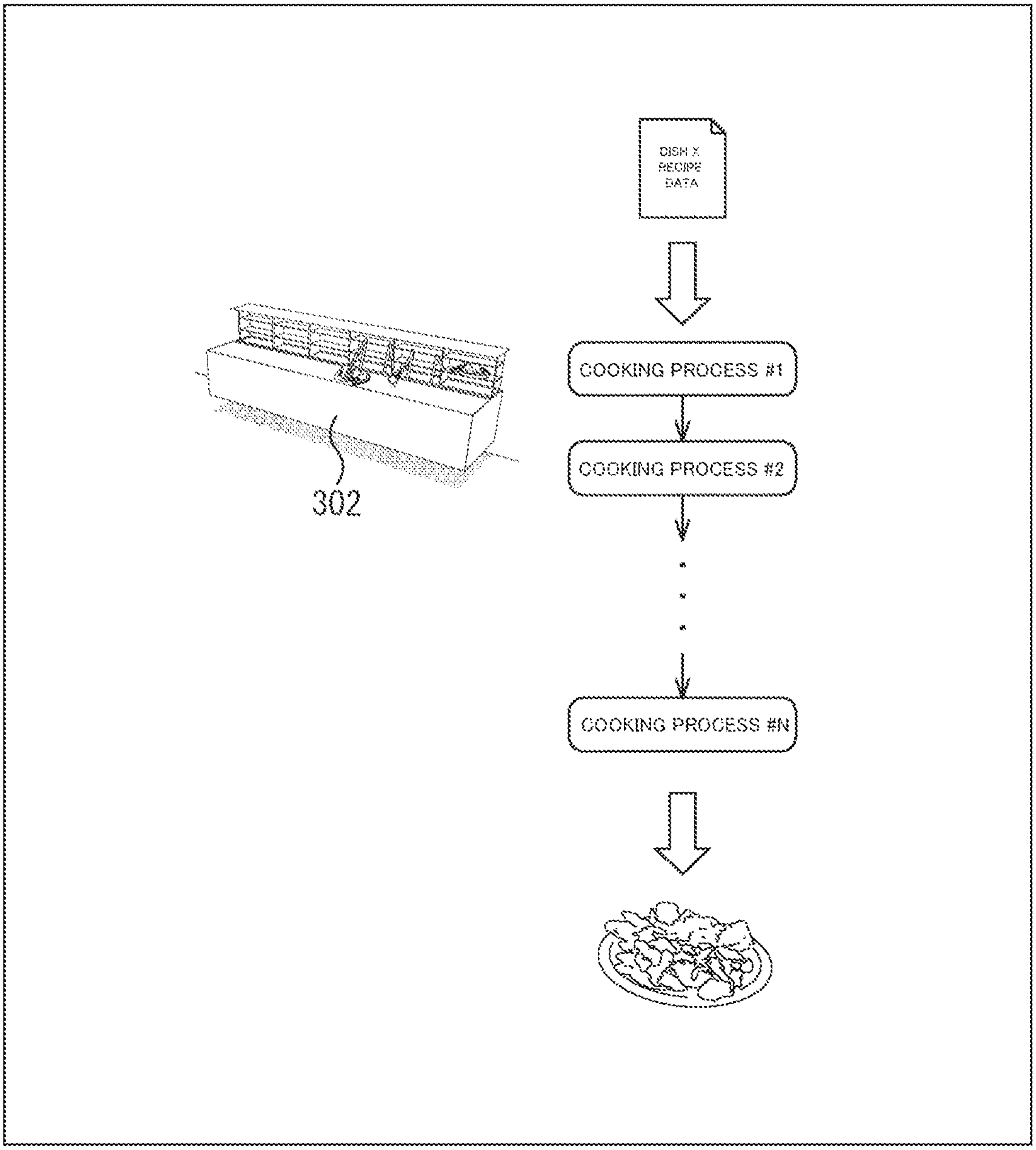
FIG. 20 is a diagram illustrating an example of a flow of reproduction of a dish based on recipe data.

FIG. 20 is a diagram illustrating an example of a flow of reproduction of a dish based on recipe data.

As illustrated in FIG. 20, reproduction of a dish by the cooking robot 302 is performed by repeating cooking on the basis of cooking operation information at each time included in cooking process data sets described in recipe data for each cooking process. One dish is completed through a plurality of cooking processes of cooking process #1 to cooking process #N.

Figure 21:
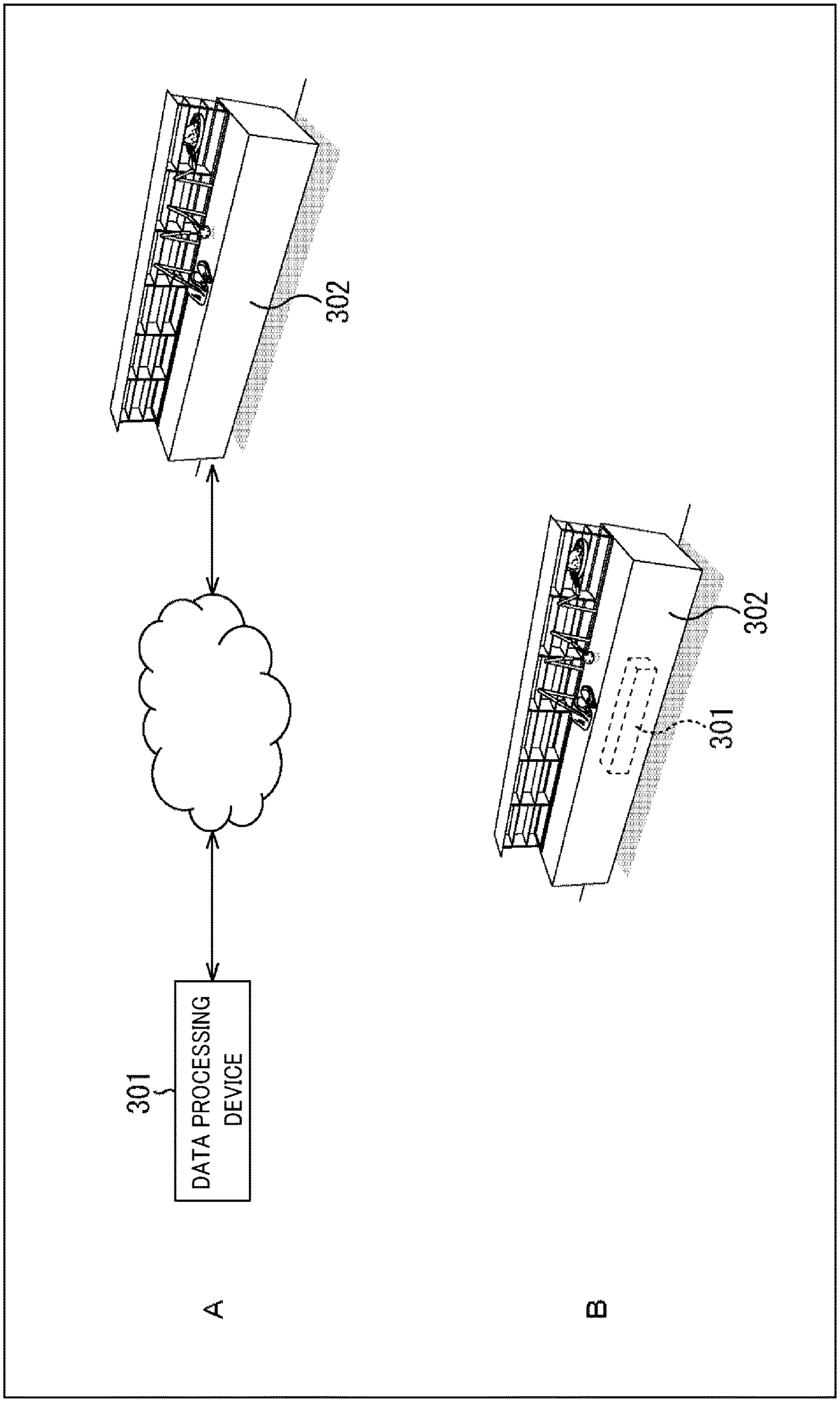
FIG. 21 is a diagram illustrating an example of arrangement of a data processing device.

FIG. 21 is a diagram illustrating an example of arrangement of the data processing device 301.

As illustrated in A of FIG. 21, the data processing device 301 may be provided, for example, as a device outside the cooking robot 302. In the example of A of FIG. 21, the data processing device 301 and the cooking robot 302 are connected through a network such as the Internet.

A command transmitted from the data processing device 301 is received by the cooking robot 302 through the network. Various types of data such as an image captured by a camera of the cooking robot 302 and sensor data measured by sensors provided in the cooking robot 302 are transmitted from the cooking robot 302 to the data processing device 301 through the network.

As illustrated in B of FIG. 21, the data processing device 301 may be provided inside a housing of the cooking robot 302. In this case, operation of each part of the cooking robot 302 is controlled according to commands generated by the data processing device 301.

Hereinafter, a case in which the data processing device 301 is provided as a device outside the cooking robot 302 will be mainly described.

Figure 22:
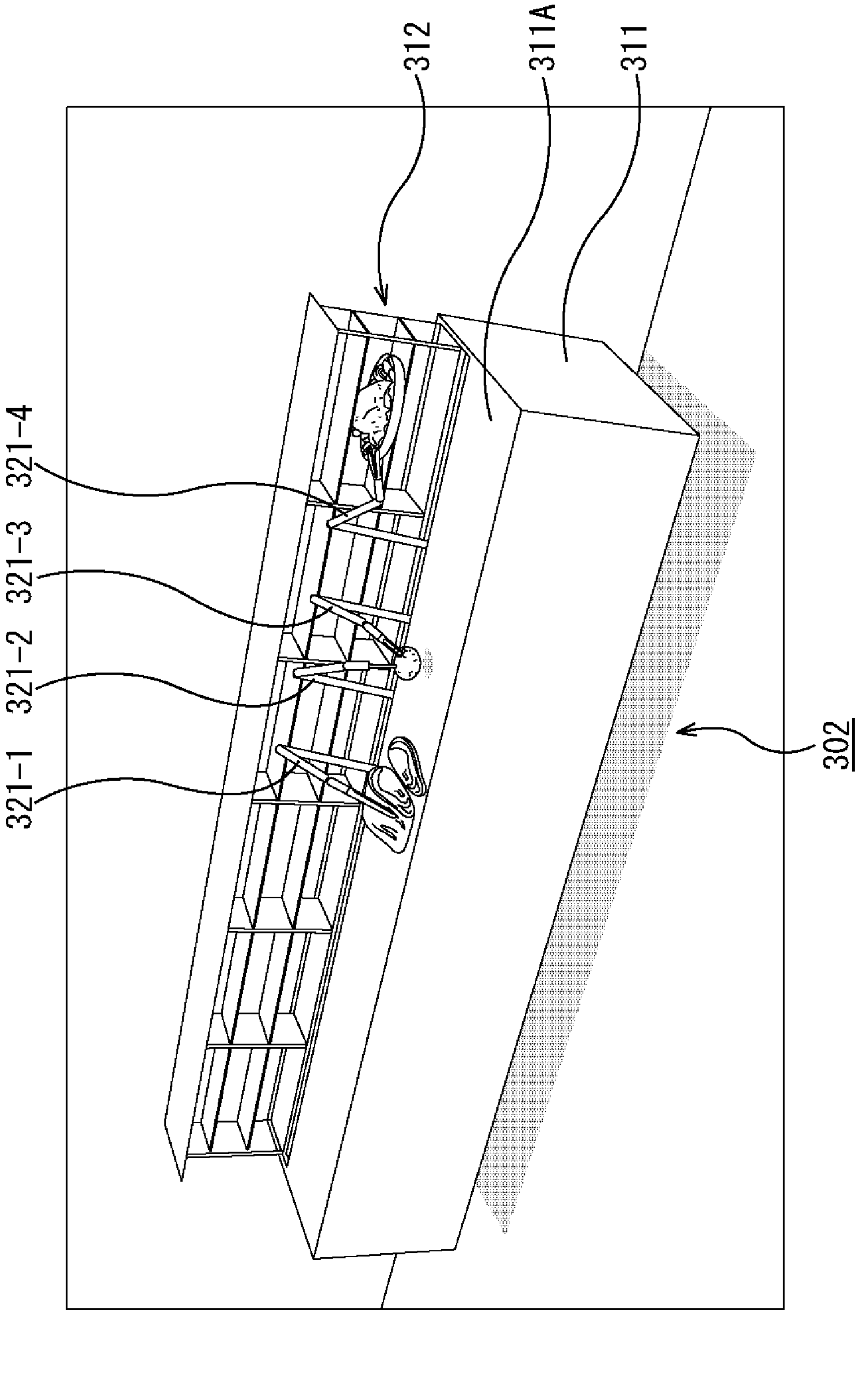
FIG. 22 is a perspective view illustrating an appearance of a cooking robot.

Appearance of cooking robot FIG. 22 is a perspective view illustrating an appearance of the cooking robot 302.

As illustrated in FIG. 22, the cooking robot 302 is a kitchen type robot having a housing 311 in a laterally long rectangular parallelepiped shape. Various components are provided in the housing 311 that is the main body of the cooking robot 302.

A cooking assistance system 312 is provided on a back side of the housing 311. Spaces partitioned by thin plate type members and formed in the cooking assistance system 312 have functions for assisting cooking according to cooking arms 321-1 to 321-4, such as a refrigerator, an oven range, and storage.

A rail is installed on a top board 311A in a longitudinal direction and the cooking arms 321-1 to 321-4 are installed on the rail. The cooking arms 321-1 to 321-4 can change positions along the rail serving as a moving mechanism.

The cooking arms 321-1 to 321-4 are robot arms configured by connecting cylindrical members through joints. Various works with respect to cooking are performed by the cooking arms 321-1 to 321-4.

A space above the top board 311A becomes a cooking space in which the cooking arms 321-1 to 321-4 perform cooking.

Although four cooking arms are illustrated in FIG. 22, the number of cooking arms is not limited to four. Hereinafter, when the cooking arms 321-1 to 321-4 need not be distinguished, they will be collectively referred to as a cooking arm 321.

Figure 23:
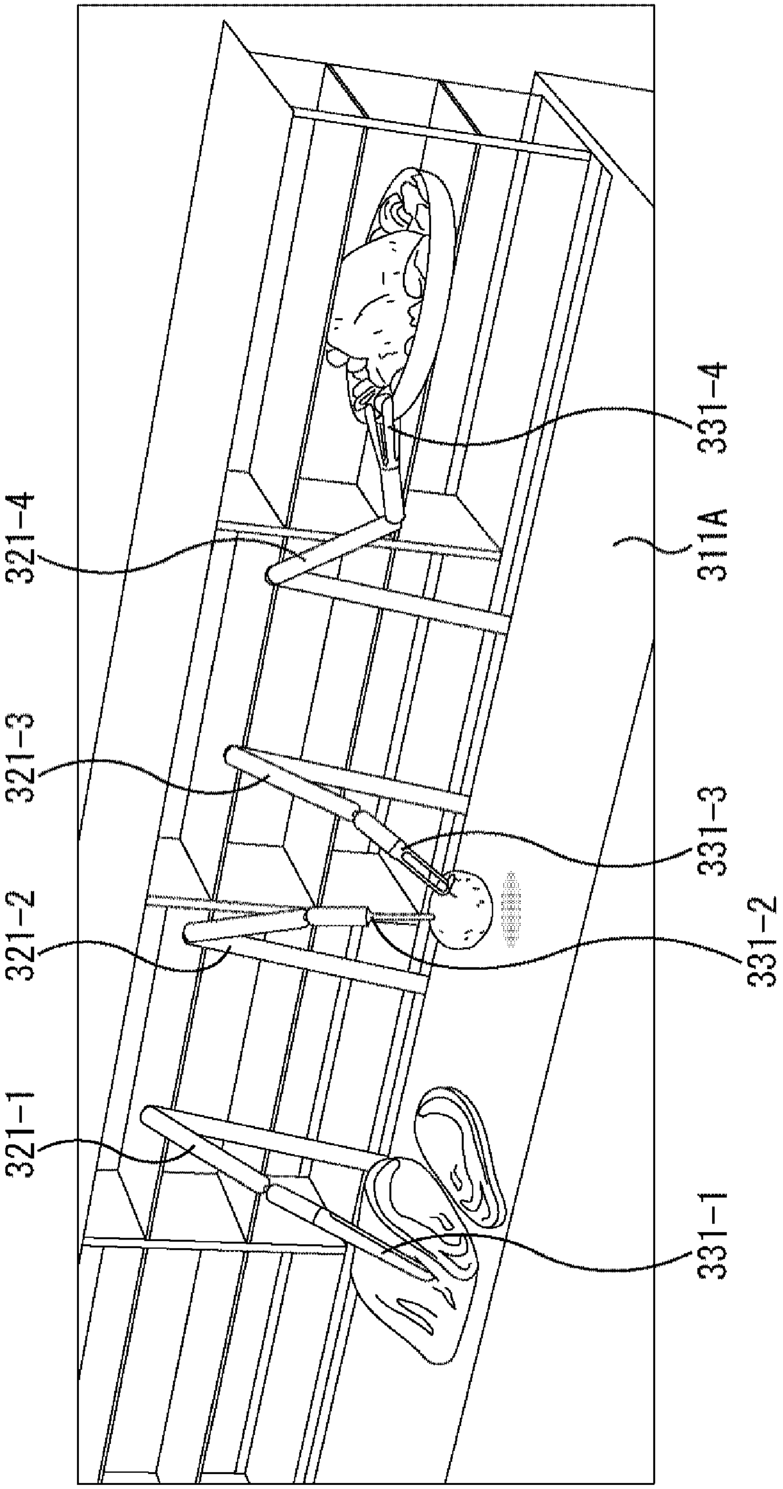
FIG. 23 is an enlarged view illustrating states of cooking arms.

FIG. 23 is an enlarged view illustrating states of the cooking arms 321.

As illustrated in FIG. 23, attachments having various cooking functions are provided at the tips of the cooking arms 321. Various attachments such as an attachment having a manipulator function (hand function) of gripping food ingredients or tableware and an attachment having a knife function of cutting food ingredients are prepared as attachments for the cooking arms 321.

In the example of FIG. 23, a knife attachment 331-1 that is an attachment having a knife function is attached to the cooking arm 321-1. A chunk of meat placed on the top board 311A is cut using the knife attachment 331-1.

A spindle attachment 331-2 that is an attachment used to fix or rotate a food ingredient is attached to the cooking arm 321-2.

A peeler attachment 331-3 that is an attachment having a peeler function of peeling a food ingredient is attached to the cooking arm 321-3.

A potato held up by the cooking arm 321-2 using the spindle attachment 331-2 is peeled by the cooking arm 321-3 using the peeler attachment 331-3. In this manner, a plurality of cooking arms 321 can perform a single work in cooperation.

A manipulator attachment 331-4 that is an attachment having a manipulator function is attached to the cooking arm 321-4. A frying pan having a chicken on it is conveyed to the space of the cooking assistance system 312 having an oven function using the manipulator attachment 331-4.

Cooking according to such cooking arms 321 is performed by appropriately switching attachments according to the content of a work. The same attachment may be attached to a plurality of cooking arms 321 in such a manner that the manipulator attachment 331-4 is attached to four cooking arms 321.

Cooking according to the cooking robot 302 is performed using not only the aforementioned attachments prepared as tools for cooking arms but also the same tools as those used by people for cooking. For example, a knife used by people may be gripped by the manipulator attachment 331-4 and cooking such as cutting a food ingredient may be performed using the knife.

Configuration of Cooking Arm

Figure 24:
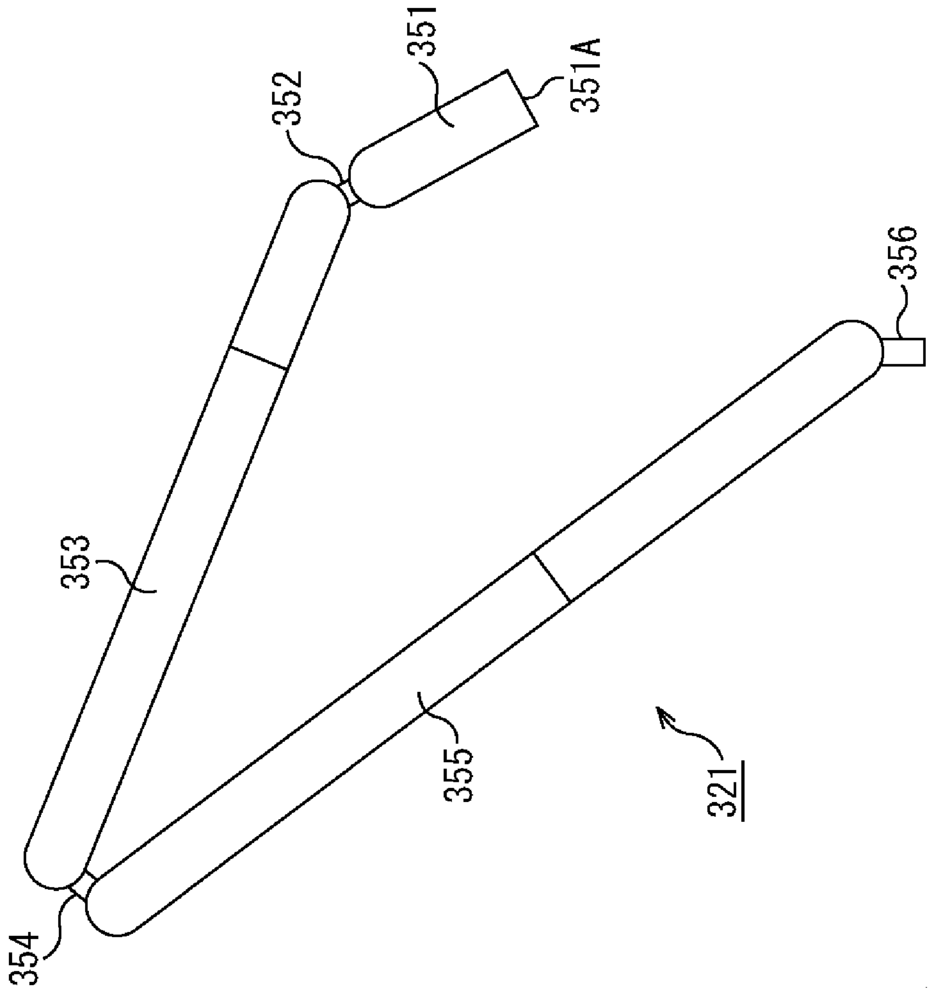
FIG. 24 is a diagram illustrating an appearance of a cooking arm.

FIG. 24 is a diagram illustrating an appearance of the cooking arm 321.

As illustrated in FIG. 24, the cooking arm 321 is constructed by connecting thin cylindrical members using hinge parts that become joints as a whole. Each hinge part is provided with a motor or the like for generating power for driving each member.

A detachable member 351, a relay member 353, and a base member 355 are sequentially provided from the tip as cylindrical members.

The detachable member 351 and the relay member 353 are connected through a hinge part 352, and the relay member 353 and the base member 355 are connected through a hinge part 354.

A detachable part 351A to/from which an attachment is attached/detached is provided at the tip of the detachable member 351. The detachable member 351 has the detachable part 351A to/from which various attachments are attached/detached and serves as a cooking function arm part that performs cooking by operating an attachment.

A detachable part 356 mounted on the rail is provided on the rear end of the base member 355. The base member 355 serves as a movement function arm part for realizing movement of the cooking arm 321.

Figure 25:
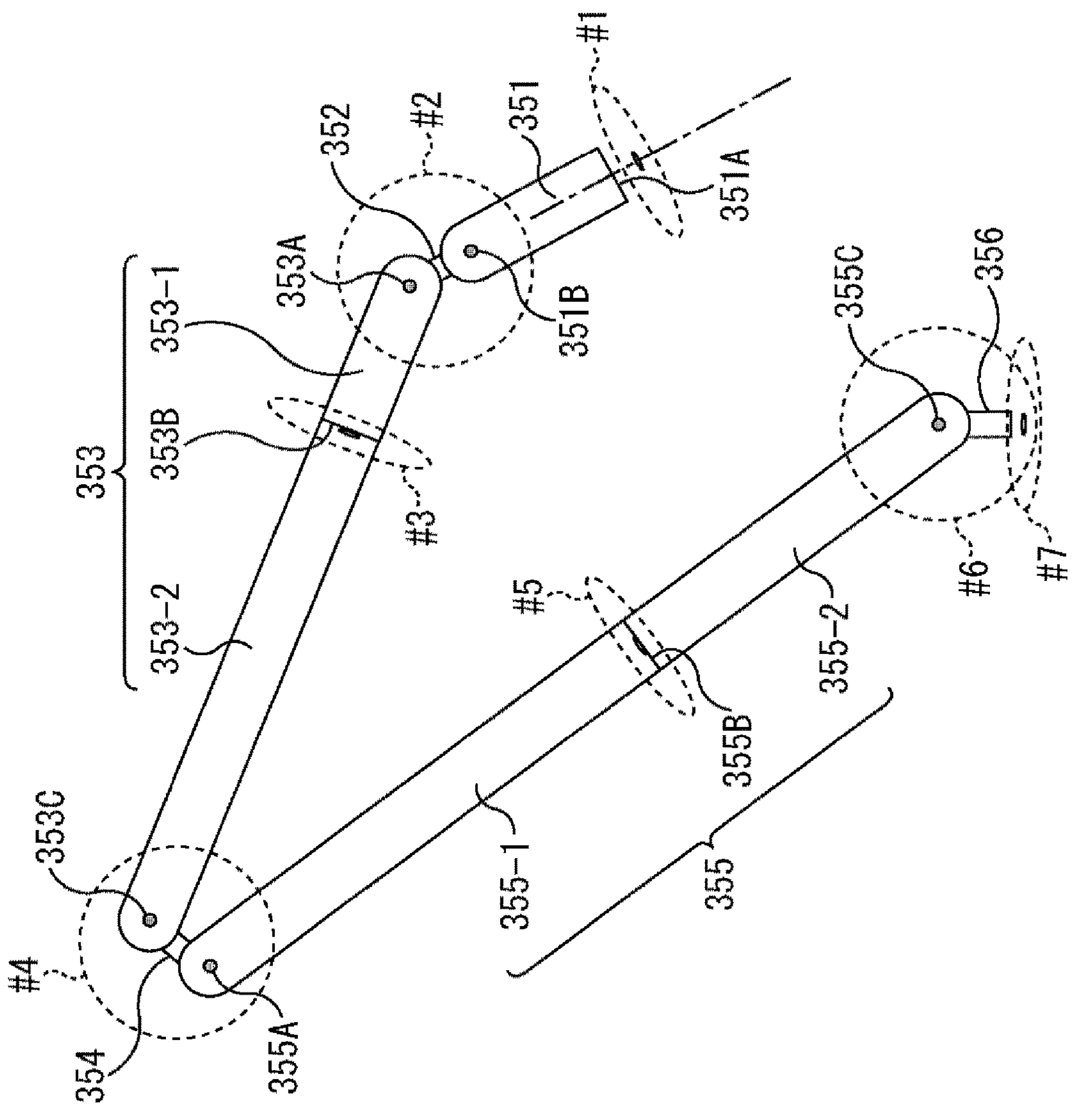
FIG. 25 is a diagram illustrating an example of a movable range of each part of the cooking arm.

FIG. 25 is a diagram illustrating an example of a movable range of each part of the cooking arm 321.

As indicated by ellipse #1, the detachable member 351 is rotatable around the central axis of the circular cross section thereof. A flat small circle indicated at the center of ellipse #1 represents the direction of the rotation axis indicated by an alternate long and short dash line.

As indicated by circle #2, the detachable member 351 is rotatable around an axis passing through an engagement part 351B engaged with the hinge part 352. In addition, the relay member 353 is rotatable around an axis passing through an engagement part 353A engaged with the hinge part 352.

Two small circles indicated inside circle #2 represent the directions (direction perpendicular to the paper surface) of the rotation axes. A movable range of the detachable member 351 around the axis passing through the engagement part 351B and a movable range of the relay member 353 around the axis passing through the engagement part 353A may be, for example, a range of 90 degrees.

The relay member 353 is separated into a member 353-1 at the tip and a member 353-2 at the rear end. As indicated by ellipse #3, the relay member 353 is rotatable around the central axis of the circular cross section thereof in a connecting part 353B between the member 353-1 and the member 353-2. Other movable parts also have the same movable range basically.

In this manner, the detachable member 351 having the detachable part 351A provided at the tip thereof, the relay member 353 connecting the detachable member 351 and the base member 355, and the base member 355 having the rear end connected to the detachable part 356 are rotatably connected through hinge parts. A motion of each movable part is controlled by a controller in the cooking robot 302 according to a command.

Figure 26:
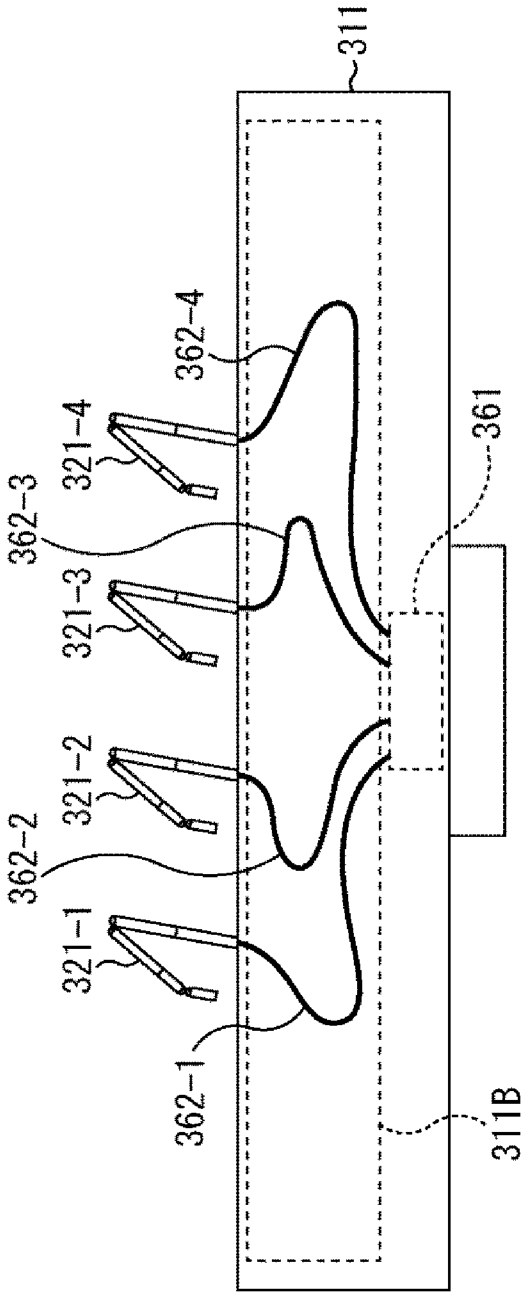
FIG. 26 is a diagram illustrating an example of connection between cooking arms and a controller.

FIG. 26 is a diagram illustrating an example of connection between cooking arms and a controller.

As illustrated in FIG. 26, the cooking arms 321 and a controller 361 are connected through wires in a space 311B formed inside the housing 311. In the example of FIG. 26, the cooking arms 321-1 to 321-4 are connected to the controller 361 through wires 362-1 to 362-4. The wires 362-1 to 362-4 having flexibility are appropriately bent depending on positions of the cooking arms 321-1 to 321-4.

Configuration of Cooking Robot 302

Figure 27:
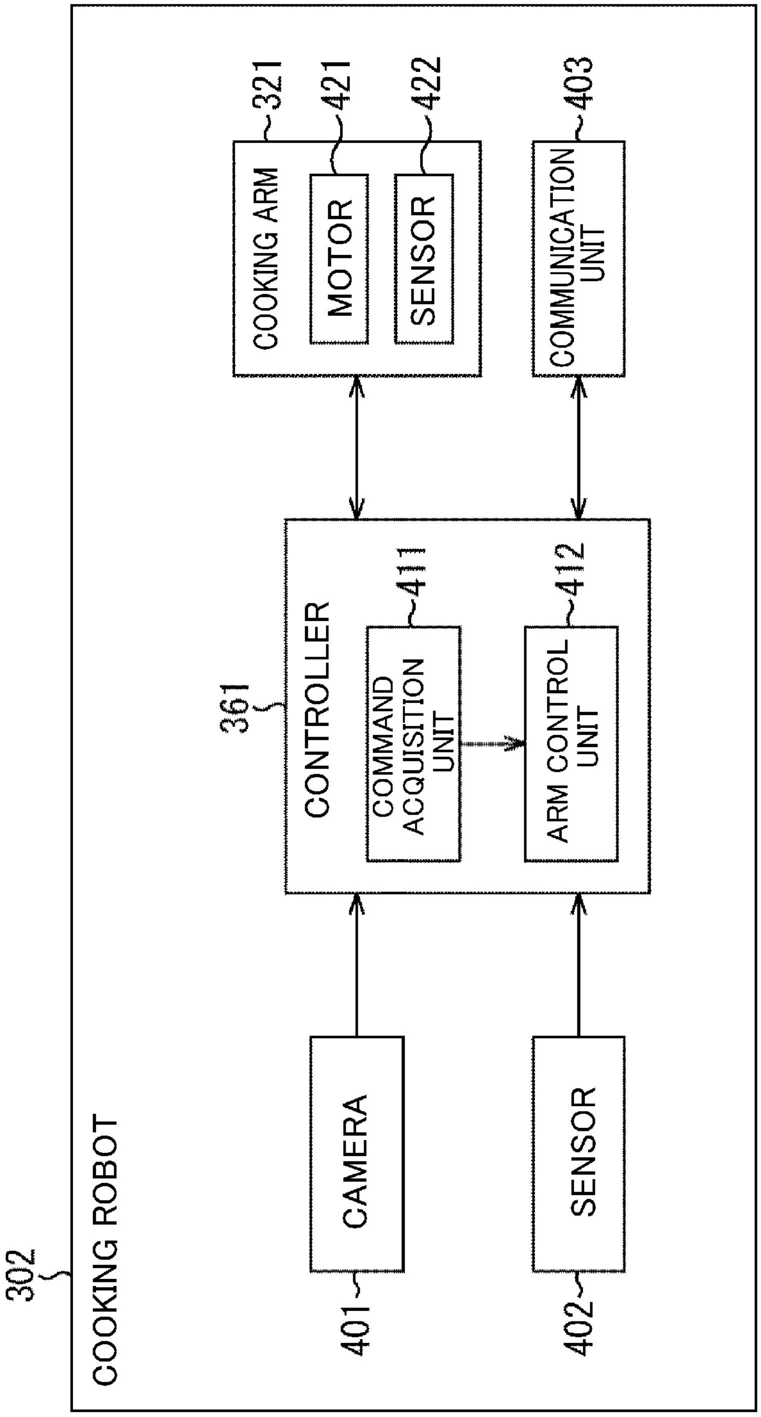
FIG. 27 is a block diagram illustrating a configuration example of the cooking robot.

FIG. 27 is a block diagram illustrating a configuration example of the cooking robot 302.

The cooking robot 302 is configured in such a manner that each part is connected to the controller 361 (FIG. 26) serving as a control device for controlling operation of the cooking robot 302. The same components among components illustrated in FIG. 27 as those described above are denoted by the same signs. Redundant description will be appropriately omitted.

A camera 401, a sensor 402, and a communication unit 403 are connected to the controller 361 in addition to the cooking arms 321.

The controller 361 includes a computer having a CPU, a ROM, a RAM, a flash memory, and the like. The controller 361 executes a predetermined program according to the CPU and controls overall operation of the cooking robot 302. The data processing device 301 may be composed of the controller 361.

For example, the controller 361 may control the communication unit 403 to transmit an image captured by the camera 401 and sensor data measured by the sensor 402 to the data processing device 301.

In the controller 361, a predetermined program is executed to realize a command acquisition unit 411 and an arm control unit 412.

The command acquisition unit 411 acquires a command transmitted from the data processing device 301 and received by the communication unit 403. The command acquired by the command acquisition unit 411 is supplied to the arm control unit 412.

The arm control unit 412 controls operation of the cooking arm 321 according to the command acquired by the command acquisition unit 411.

The camera 401 captures an image of a state around the cooking robot 302 and outputs the captured image to the controller 361. The camera 401 is provided at various positions such as the front side of the cooking assistance system 312 and the tip of the cooking arm 321.

The sensor 402 includes various sensors such as a temperature/humidity sensor, a pressure sensor, an optical sensor, a distance sensor, a motion sensor, a positioning sensor, and a vibration sensor. Measurement according to the sensor 402 is performed at predetermined intervals. Sensor data representing measurement results of the sensor 402 is supplied to the controller 361.

The camera 401 and the sensor 402 may be provided at positions separated from the housing 311 of the cooking robot 302.

The communication unit 403 is a wireless communication module such as a wireless LAN module or a portable communication module corresponding to LTE (Long Term Evolution). The communication unit 403 performs communication with the data processing device 301 and an external device such as a server on the Internet.

As illustrated in FIG. 27, a motor 421 and a sensor 422 are provided in the cooking arm 321.

The motor 421 is provided at each joint of the cooking arm 321. The motor 421 performs an operation of rotating around an axis according to control of the arm control unit 412. An encoder that measures the amount of rotation of the motor 421, a driver that adaptively controls rotation of the motor 421 on the basis of a measurement result of the encoder, and the like are also provided at each joint.

The sensor 422 may include, for example, a gyro sensor, an acceleration sensor, a touch sensor, and the like. The sensor 422 measures an angular velocity, an acceleration, and the like of each joint during operation of the cooking arm 321 and outputs information representing measurement results to the controller 361. Sensor data representing a measurement result of the sensor 422 is also appropriately transmitted from the cooking robot 302 to the data processing device 301.

Configuration of Data Processing Device 301

Figure 28:
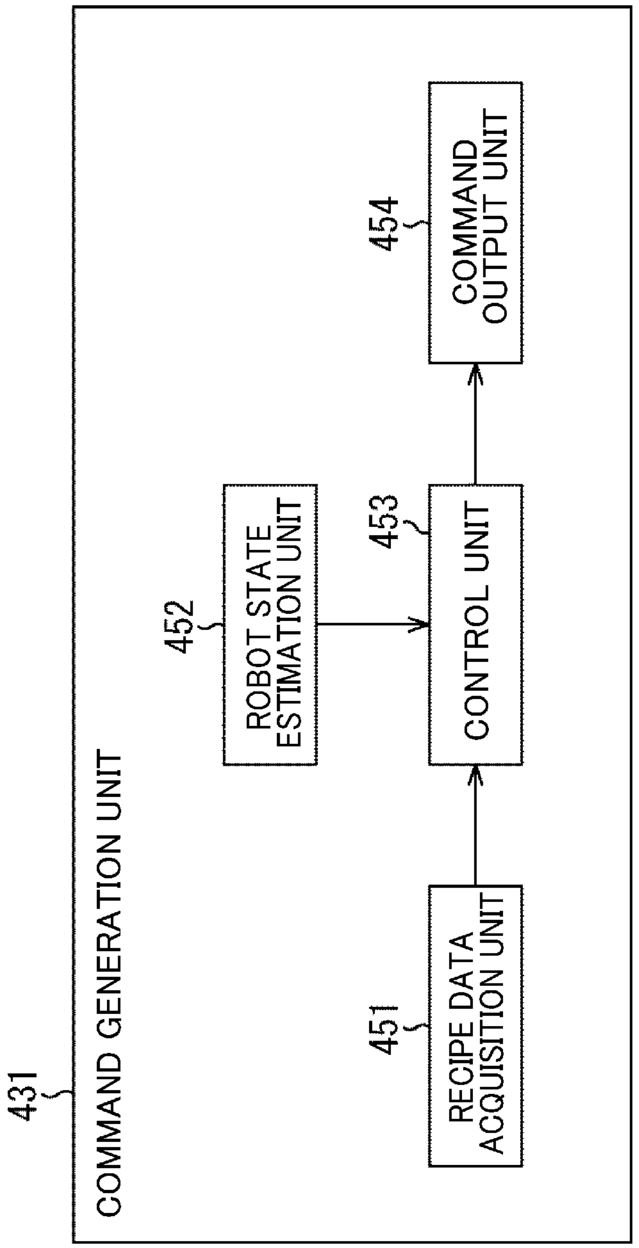
FIG. 28 is a block diagram illustrating a functional configuration example of a data processing device.

FIG. 28 is a block diagram illustrating a functional configuration example of the data processing device 301.

At least some of the functional units illustrated in FIG. 28 are realized by causing the CPU of the data processing device 301 to execute a predetermined program.

As illustrated in FIG. 28, a command generation unit 431 is realized in the data processing device 301. The command generation unit 431 includes a recipe data acquisition unit 451, a robot state estimation unit 452, a control unit 453, and a command output unit 454.

The recipe data acquisition unit 451 acquires recipe data newly generated in the information processing device 1 or the like and outputs the recipe data to the control unit 453. The information processing unit 151 (FIG. 16) having the recipe generation function may be provided in the recipe data acquisition unit 451.

The robot state estimation unit 452 receives an image and sensor data transmitted from the cooking robot 302. An image captured by the camera of the cooking robot 302 and sensor data measured by sensors provided at predetermined positions of the cooking robot 302 are transmitted from the cooking robot 302 at predetermined intervals. A state around the cooking robot 302 is reflected in an image captured by the camera of the cooking robot 302.

The robot state estimation unit 452 estimates states around the cooking robot 302 and states of cooking processes, such as states of the cooking arms 321 and states of food ingredients, by analyzing the image and the sensor data transmitted from the cooking robot 302. Information representing states around the cooking robot 302, and the like estimated by the robot state estimation unit 452 is supplied to the control unit 453.

The control unit 453 generates a command for controlling the cooking robot 302 on the basis of cooking process data sets described in the recipe data supplied from the recipe data acquisition unit 451. For example, a command for causing the cooking arm 321 to perform an operation represented by cooking operation information included in the cooking process data set may be generated.

A command is generated with reference to states around the cooking robot 302, and the like estimated by the robot state estimation unit 452. The command generated by the control unit 453 is supplied to the command output unit 454.

The command output unit 454 transmits the command generated by the control unit 453 to the cooking robot 302.

Operation of Data Processing Device 301

Figure 29:
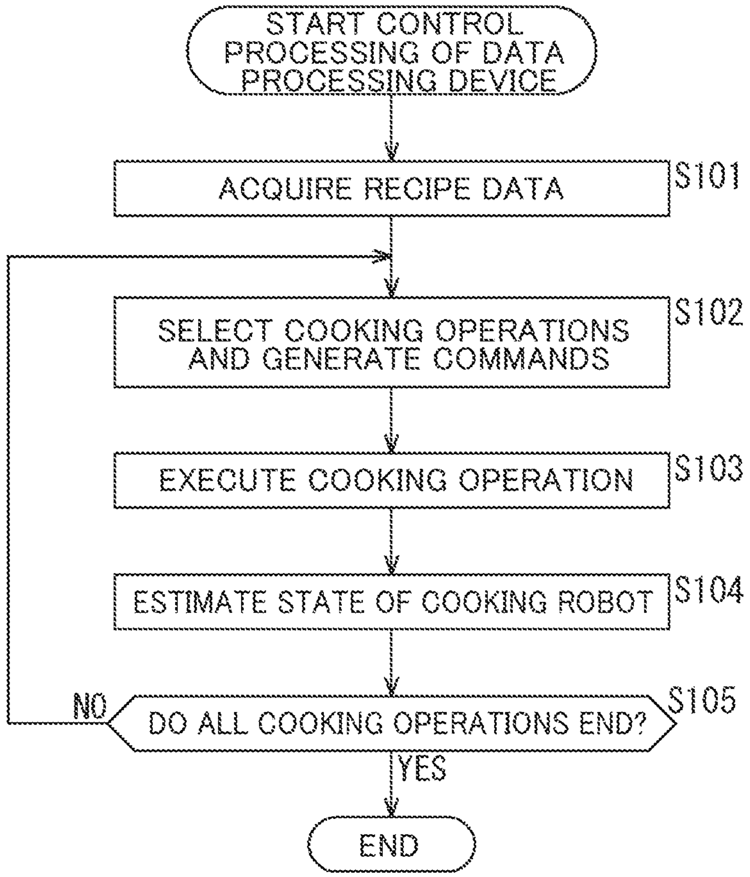
FIG. 29 is a flowchart for describing processing of the data processing device.

Processing of the data processing device 301 to control operation of the cooking robot 302 will be described with reference to the flowchart of FIG. 29.

In step S101, the recipe data acquisition unit 451 acquires recipe data representing a recipe generated by the information processing device 1 or the like.

In step S102, the control unit 453 selects a predetermined cooking operation on the basis of cooking process data sets described in the recipe data and generates a command for causing the selected cooking operation to be performed. For example, the cooking process data sets are selected in order of cooking processes, and cooking operations included in the selected cooking processes are selected in order of execution.

In step S103, the command output unit 454 transmits the command to the cooking robot 302 to cause the cooking robot 302 to execute cooking operations.

In step S104, the robot state estimation unit 452 estimates a state of the cooking robot 302.

In step S105, the control unit 453 determines whether all cooking operations end. When it is determined that all cooking operations do not end in step S105, processing returns to step S102, the next cooking operation is selected and the above-described processing is repeated.

When it is determined that all cooking operations end in step S105, processing ends. Here, a dish is completed on the basis of new recipe data generated by the information processing device 1 or the like.

In this manner, recipe data for controlling the robot that performs cooking using cooking arms can be generated by the information processing device 1.

When a recipe of blending an amount α of sake Sake_A and an amount of ß of sake Sake_B is generated as described above, for example, commands for causing the following cooking operations to be performed are output to the cooking robot 302. Each operation is performed by the cooking arm 321.

1. sake Sake_A is prepared.
2. sake Sake_B is prepared.
3. A cup is prepared.

4. sake Sake_A is poured into the cup by the amount α.
5. sake Sake_B is poured into the cup by the amount ß.
6. The cup is shaken in a state in which it is held up to mix sake Sake_A and sake Sake_B.
7. The cup is handed over to a user of the cooking robot 302.

Such a series of operations is performed to provide new sake with a flavor designated by a chef to the user of the cooking robot 302.

Figure 30:
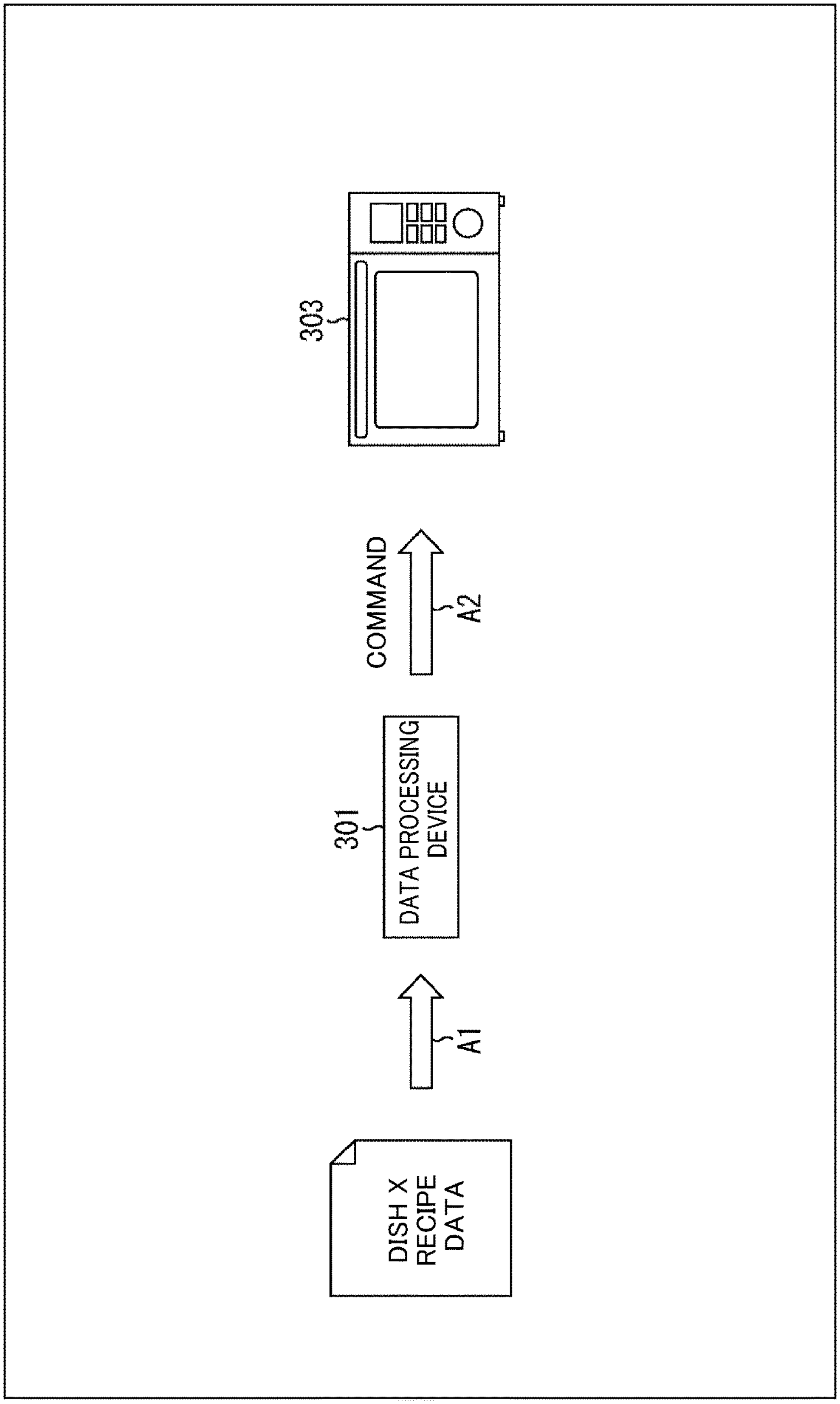
FIG. 30 is a diagram illustrating another configuration example of the control system.

FIG. 30 is a diagram illustrating another configuration example of a control system.

In the control system illustrated in FIG. 30, electronic cooking equipment 303 such as a microwave oven instead of the cooking robot 302. The electronic cooking equipment 303 executes a cooking operation according to a command supplied from the data processing device 301 to perform cooking.

In this manner, recipe data can be used to control various apparatuses that automatically perform a cooking operation.

[Other Examples]

Configuration Example of Computer

The above-described series of processes can be performed by hardware or performed by software. When the series of processing is performed by software, a program for the software is installed in a computer embedded in dedicated hardware, a general-purpose personal computer, or the like.

The installed program is provided by being recorded in a removable medium 111 illustrated in FIG. 15, which is composed of an optical disc (a compact disc-read only memory (CD-ROM), a digital versatile disc (DVD), or the like), a semiconductor memory, or the like. In addition, the program may be provided through a wired or wireless transmission medium such as a local area network, the Internet or digital broadcast. The program can be installed in the ROM 102 or the storage unit 108 in advance.

The program executed by the computer may be a program that performs processing chronologically in the procedure described in the present specification or may be a program that performs processing at a necessary timing such as in parallel or upon being called.

In the present specification, a system is a collection of a plurality of constituent elements (devices, modules (components), or the like) and all the constituent elements may be located or not located in the same casing. Therefore, a plurality of devices housed in separate housings and connected via a network, and one device in which a plurality of modules are housed in one housing are both systems.

The advantages described in the present specification are merely exemplary and not limited, and other advantages may be obtained.

The embodiments of the present technology are not limited to the above-described embodiments, and various modifications can be made without departing from the gist of the present technology.

For example, the present technology can employ a configuration of cloud computing in which one function is shared and processed in common by a plurality of devices via a network.

Further, the respective steps described in the above-described flowchart can be executed by one device or in a shared manner by a plurality of devices.

Furthermore, in a case where a plurality of kinds of processing are included in a single step, the plurality of kinds of processing included in the single step may be executed by one device or by a plurality of devices in a shared manner.

REFERENCE SIGNS LIST

1 Information processing device
21 Flavor subjective information DB
22 Sensing information DB
23 Chemical structure information DB
151 Information processing unit
161 Recipe generation unit
162 Presentation unit
171 Recipe generation server
301 Data processing device
302 Cooking robot

The invention claimed is:

1. An information processing device comprising:
circuitry configured to
generate a new recipe based on
chemical structure information representing chemical structures of food ingredients used for cooking,
sensing information obtained by measuring flavors of food ingredients using a sensor, and
flavor subjective information representing subjective evaluation of people with respect to flavors of food ingredients, and
generate commands for causing a cooking robot to execute cooking operations,
wherein the circuitry generates the new recipe based on transformation information with respect to a same food ingredient.

2. The information processing device according to claim 1,
wherein the circuitry generates the new recipe based on the transformation information representing mutual relations between the chemical structure information, the sensing information, and the flavor subjective information with respect to the same food ingredient.

3. The information processing device according to claim 1,
wherein the circuitry generates the new recipe using food ingredients included in a combination of food ingredients selected based on chemical structures represented by the chemical structure information.

4. The information processing device according to claim 3,
wherein each of the chemical structure information, the sensing information, and the flavor subjective information is represented by a vector having a plurality of items as elements.

5. The information processing device according to claim 4,
wherein the circuitry selects a combination of food ingredients by performing a vector operation of multiplying a vector forming chemical structure information of each food ingredient that is a combination target by a coefficient corresponding to a combination amount of each food ingredient.

6. The information processing device according to claim 1,
wherein the circuitry generates the new recipe in which the chemical structure information, the sensing information, and the flavor subjective information with respect to food ingredients used for cooking performed according to the new recipe are associated.

7. The information processing device according to claim 1,
wherein the circuitry generates the commands for causing the cooking robot to execute the cooking operations according to each process described in the new recipe based on recipe data representing the new recipe generated by the circuitry.

8. The information processing device according to claim 1, wherein the chemical structure information is information obtained by measuring chemical structures of food ingredients using an analyzer.

9. The information processing device according to claim 1, wherein the sensing information is information obtained by measuring flavors of food ingredients using a flavor measuring instrument.

10. The information processing device according to claim 1, wherein the flavor subjective information is information representing a subjective evaluation value of a flavor from a person who ate a food ingredient.

11. The information processing device according to claim 1, wherein the transformation information is used to transform a value of the sensing information into a value of the chemical structure information.

12. An information processing method, executed by at least one processor of an information processing device, the method comprising:

generating a new recipe based on chemical structure information representing chemical structures of food ingredients used for cooking, sensing information obtained by measuring flavors of food ingredients using a sensor, and flavor subjective information representing subjective evaluation of people with respect to flavors of food ingredients corresponding to the flavors of the food ingredients measured using the sensor; and generating commands for causing a cooking robot to execute cooking operations, wherein the new recipe is generated based on transformation information with respect to a same food ingredient.

* * * * *